US007439338B2

(12) United States Patent
Millward et al.

(10) Patent No.: US 7,439,338 B2
(45) Date of Patent: Oct. 21, 2008

(54) BETA-DIKETIMINATE LIGAND SOURCES AND METAL-CONTAINING COMPOUNDS THEREOF, AND SYSTEMS AND METHODS INCLUDING SAME

(75) Inventors: Dan Millward, Boise, ID (US); Timothy A. Quick, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 581 days.

(21) Appl. No.: 11/169,065

(22) Filed: Jun. 28, 2005

(65) Prior Publication Data

US 2006/0292303 A1    Dec. 28, 2006

(51) Int. Cl.
  C07F 5/00    (2006.01)
  C07F 3/00    (2006.01)
  C23C 16/00   (2006.01)
(52) U.S. Cl. .............................. 534/15; 556/32; 556/34; 556/35; 427/252
(58) Field of Classification Search .................. 556/32, 556/34, 35; 534/15; 427/252
See application file for complete search history.

(56) References Cited

U.S. PATENT DOCUMENTS

| | | | |
|---|---|---|---|
| 5,256,244 | A | 10/1993 | Ackerman |
| 5,972,430 | A | 10/1999 | DiMeo, Jr. et al. |
| 6,225,237 | B1 | 5/2001 | Vaartstra |
| 6,455,717 | B1 | 9/2002 | Vaartstra |
| 6,682,602 | B2 | 1/2004 | Vaartstra |
| 6,828,256 | B2 | 12/2004 | Vaartstra |
| 6,939,578 | B2 | 9/2005 | Bradley et al. |
| 7,020,981 | B2 | 4/2006 | Shero et al. |
| 2002/0187578 | A1 | 12/2002 | Hong |
| 2003/0113480 | A1 | 6/2003 | Kil et al. |
| 2004/0247905 | A1 | 12/2004 | Bradley et al. |
| 2005/0003075 | A1 | 1/2005 | Bradley et al. |
| 2005/0107283 | A1 | 5/2005 | Bradley et al. |
| 2005/0158479 | A1 | 7/2005 | Bradley et al. |
| 2005/0227007 | A1 | 10/2005 | Bradley et al. |
| 2006/0292841 | A1 | 12/2006 | Quick |
| 2006/0292873 | A1 | 12/2006 | Millward et al. |
| 2007/0234962 | A1* | 10/2007 | Suzuki et al. ............... 118/726 |

FOREIGN PATENT DOCUMENTS

| | | |
|---|---|---|
| DE | 42 02 889 A 1 | 8/1993 |
| DE | 42 02 899 A1 | 8/1993 |
| WO | WO 03/095701 | 11/2003 |
| WO | WO 2007/002672 | 1/2007 |
| WO | WO 2007/002673 | 1/2007 |
| WO | WO 2007/002674 | 1/2007 |

OTHER PUBLICATIONS

Hitchcock et al., Chemical Communications, Issue No. 10, pp. 1142-1143 (2003).*

Barluenga et al., "Reaction of Fischer alkynylcarbene complexes with 1-azadiene derivatives: unexpected formation of 3, 4-dihydropyridines," *New Journal of Chemistry*, 2001; 25:8-10 (3 pgs). First published as an Advanced Article on the web Nov. 15, 2000.

Gusev et al., "Reaction of Methyldiacetylene with Primary Amines," *Bulletin of the Academy of Sciences of the USSR, Division Chemical Sciences (English Translation)*, 1974; 23:194-195 (2 pgs).

Knorr et al., "Configurational stability and reduced $^1$H-NMR shifts of (pseudo)tetrahedral nickel(II) bis-chelates of 1,3-diimines [1],"English language translation (19 pgs) of *Chem. Ber.*, 1981; 114:2104-2115 in German (12 pgs).

Park et al., "Routes to N, N'—Unsymmetrically Substituted 1, 3-Diketimines," *Journal of Organic Chemistry*, 2005; 70:2075-2081 (7 pgs). Published on Web Feb. 9, 2005.

Rische et al., "New Tungsten(VI) Guanidinato Complexes: Synthesis, Characterization, and Application in Metal-Organic Chemical Vapor Deposition of Tungsten Nitride Thin Films," *Chem. Mater.*, 2006; 18:6075-6082 (8 pgs). Published on the web Nov. 15, 2006.

Schroth et al., "Nucleophilic addition of amines to diacetylene and 1 amniobut-1-en-3-ine," English language translation (4 pgs) of *Z. Chem.*, 1969; 9(3):110-111 (2 pgs).

U.S. Appl. No. 11/168,160, filed Jun. 28, 2005, Quick, Timothy.
U.S. Appl. No. 11/169,082, filed Jun. 28, 2005, Millward et al.

Bourget-Merle et al., "The Chemistry of β-Diketiminatometal Complexes," *Chem. Rev.*, 2002;102:3031-3065. Published on Web Aug. 24, 2002.

Chisholm et al., "Lactide polymerization by well-defined calcium coordination complexes: comparisons with related magnesium and zinc chemistry," *Chem Commun. (Camb.)*, Jan. 7, 2003; 1:48-49. First published as an Advance Article on the Web Dec. 5, 2002.

Clegg et al., "Alkaline Earth Diazapentadienyl Compounds: Structure of [Ba$_2${(C$_6$H$_{11}$)NC(Me)CHC(Me)-N(C$_6$H$_{11}$)}$_3${(SiMe$_3$)$_2$N}]," *Angew. Chem. Int. Ed*, 1998;37(6):796-797.

Cui et al., "Synthesis and Structure of a Monomeric Aluminum(I) Compound [{HC(CMeNAr)$_2$}Al] (Ar=2,6iPr$_2$C$_6$H$_3$): A Stable Aluminum Analogue of a Carbene," *Agnew Chem. Int. Ed.*, 2000;39(23): 4274-4276.

(Continued)

*Primary Examiner*—P. Nazario Gonzalez
(74) *Attorney, Agent, or Firm*—Mueting, Raasch & Gebhardt, P.A.

(57) ABSTRACT

The present invention provides metal-containing compounds that include at least one β-diketiminate ligand, and methods of making and using the same. In certain embodiments, the metal-containing compounds include at least one β-diketiminate ligand with at least one fluorine-containing organic group as a substituent. In other certain embodiments, the metal-containing compounds include at least one β-diketiminate ligand with at least one aliphatic group as a substituent selected to have greater degrees of freedom than the corresponding substituent in the β-diketiminate ligands of certain metal-containing compounds known in the art. The compounds can be used to deposit metal-containing layers using vapor deposition methods. Vapor deposition systems including the compounds are also provided. Sources for β-diketiminate ligands are also provided.

20 Claims, 2 Drawing Sheets

OTHER PUBLICATIONS

Eisenstein et al., "Mono-, Di-, and Trianionic β-Diketiminato Ligands: A Computational Study and the Synthesis and Structure of [(YbL)$_3$(THF)], L=[{N(SiMe$_3$)C(Ph)}$_2$CH]," *J Am Chem Soc.*, 2003;125:10790-10791. Publised on Web Aug. 15, 2003.

El-Kaderi et al., "Sandwich Complexes of the Heavier Alkaline Earth Metals Containing η$^5$-β-Diketiminato Ligand Sets,"*Organometallics*, 2004;23: 4995-5002. Published on Web Sep. 14, 2004.

Franceschini et al., "Volatile β-Ketoiminato- and β-Diketiminato-Based Zirconium Complexes as Potential MOCVD Precursors," *Inorganic Chemistry*, 2003;42(22): 7273-7282. Published on Web Oct. 2, 2003.

Harder, Sjoerd, "Homoleptic β-Diketiminato Complexes of the Alkaline-Earth Metals: Trends in the Series Mg, Ca, Sr, and Ba," *Organometallics*, 2002;21:3782-3787. Published on Web Aug. 9, 2002.

Harder, Sjoerd, "Intramolecular C-H Activation in Alkaline-Earth Metal Complexes," *Angew Chem Int Ed*, 2003;42:3430-3434.

Hardman et al., "Synthesis and characterization of the monomer Ga{(NDippCMe)$_2$CH} (Dipp=C$_6$H$_3$Pr$^i_2$-2,6): a low valent gallium(I) carbene analogue," *Chem. Comm.*, 2000:1991-1992. First published as an Advance Article on the Web Sep. 27, 2000.

Hawley G.G., "The Condensed Chemcial Dictionary," *10th Edition*, 1981, Van Norstrand Reinhold Co., New York, 225-26.

Hill and Hitchcock, "Bis(Phosphinimino)methyl derivatives of Ca, Sr and Ba: facile access to heavier alkaline earth organometallic chemistry,"*Chem Commun. (Camb.)*, 2003;14:1758-1759. First published as an Advance Article on the Web Jun. 18, 2003.

Hitchcock et al., "New reactions of β-diketiminatolanthanoid complexes: sterically induced self-deprotonation of β-diketiminato ligands," *Chem Commun.*, 2005:951-953. First Published as an Advance Article on the Web Jan. 6, 2005.

Holland et al., "Electronically Unsaturated Three-Coordinate Chloride and Methyl Complexes of Iron, Cobalt, and Nickel," *J Am. Chem. Soc.*, 2002;124:14416-14424. Published on the Web Nov. 8, 2002.

Li et al., "Synthesis and Characterization of Copper(I) Amidinates as Precursors for Atomic Layer Deposition (ALD) of Copper Metal," *Inorganic Chemistry*, 2005;44: 1728-1735. Published on the Web Feb. 3, 2005.

Piers and Emslie, "Non-cyclopentadienyl ancillaries in organogroup 3 metal chemistry: a fine balance in ligand design," *Coordination Chemistry Reviews*, 2002;233-234:131-155.

Shimokawa and Itoh, "The First β-Diketiminate-Ag(I) Complexes. Macrocyclic Dinulcear and Tetranuclear Ag(I)-Complexes and Linear Coordination Polymer Ag(I)-Complex," *Inorganic Chemistry*, 2005;44: 3010-3012. Published on the Web Apr. 5, 2005.

Vehkamäki et al., "Growth of SrTiO$_3$ and BaTiO$_3$ Thin Films by Atomic Layer Deposition," *Electrochemical and Solid-State Letters*, 1999;2(10): 504-506. Available electronically Aug. 5, 1999.

El-Kaderi et al., "Synthesis, Structure, and Ligand Redistribution Equilibria of Mixed Ligand Complexes of the Heavier Group 2 Elements Containing Pyrazolato and β-Diketiminato Ligands," *Eur. J. Inorg. Chem.*, 2005:2081-2088. (published online Jun. 1, 2005.

Ashton et al., "A Regioselective route to 3-Alkyl-l-aryl-1*H*-pyrazole-5-carboxylates: synthetic studies and structural assignments," *Journal of Heterocyclic Chemistry*, Mar. 1993;30(2):307-311.

Coe et al., "Reactions of tetrafluoroethene oligomers. Part 9. Some reactions of perfluoro-(1-ethyl-1-methylpropyl)(s-butyl)ethanolide (an α-Lactone)," *Journal of the Chemical Society, Perkin Transactions I*, 1989;6:1097-1104.

El-Kaderi et al., "Complexes of the heavier alkaline earth metals containing β-diketiminato and iodide ligand sets," *Polyhedron*, Jan. 23, 2006;25(2):224-234 (Available online Aug. 11, 2005).

England et al., "Reactions of amines with a dimer hexafluoropropene and with a perfluorovinly sulfide prepared with hexafluoropropene," *Journal of Fluorine Chemistry*, 1981;28(2784):265-288.

Yakimovich et al., "Tautomerism in the series of products from the condensation of β-ketoaldehydes with N,N-disubstituted hydrazines," *Journal of Organic Chemistry of the USSR*, 1990;26(12):2174-2181.

\* cited by examiner

BETA-DIKETIMINATE LIGAND SOURCES AND METAL-CONTAINING COMPOUNDS THEREOF, AND SYSTEMS AND METHODS INCLUDING SAME

BACKGROUND

The scaling down of integrated circuit devices has created a need to incorporate high dielectric constant materials into capacitors and gates. The search for new high dielectric constant materials and processes is becoming more important as the minimum size for current technology is practically constrained by the use of standard dielectric materials. Dielectric materials containing alkaline earth metals can provide a significant advantage in capacitance compared to conventional dielectric materials. For example, the perovskite material $SrTiO_3$ has a disclosed bulk dielectric constant of up to 500.

Unfortunately, the successful integration of alkaline earth metals into vapor deposition processes has proven to be difficult. For example, although atomic layer deposition (ALD) of alkaline earth metal diketonates has been disclosed, these metal diketonates have low volatility, which typically requires that they be dissolved in organic solvent for use in a liquid injection system. In addition to low volatility, these metal diketonates generally have poor reactivity, often requiring high substrate temperatures and strong oxidizers to grow a film, which is often contaminated with carbon. Other alkaline earth metal sources, such as those including substituted or unsubstituted cyclopentadienyl ligands, typically have poor volatility as well as low thermal stability, leading to undesirable pyrolysis on the substrate surface.

New sources and methods of incorporating high dielectric materials are being sought for new generations of integrated circuit devices.

SUMMARY OF THE INVENTION

The present invention provides metal-containing compounds (i.e., metal-containing complexes) that include at least one β-diketiminate ligand, and methods of making and using, and vapor deposition systems including the same. Certain metal-containing compounds having at least one β-diketiminate ligand are known in the art. In such certain known metal-containing compounds, the β-diketiminate ligand has isopropyl substituents on both nitrogen atoms, or tert-butyl substituents on both nitrogen atoms. See, for example, El-Kaderi et al., *Organometallics*, 23:4995-5002 (2004). The present invention provides metal-containing compounds (i.e., metal-containing complexes) including at least one β-diketiminate ligand, which can have desirable properties (e.g., one or more of higher vapor pressure, lower melting point, and lower sublimation point) for use in vapor deposition methods.

In certain embodiments, the present invention provides metal-containing compounds having at least one β-diketiminate ligand with at least one fluorine-containing organic group as a substituent. In other certain embodiments, the present invention provides metal containing compounds having at least one β-diketiminate ligand with at least one aliphatic group as a substituent selected to have greater degrees of freedom than the corresponding substituent in the β-diketiminate ligands of certain metal-containing compounds known in the art.

In one aspect, the present invention provides a method of forming a metal-containing layer on a substrate (e.g., a semiconductor substrate or substrate assembly) using a vapor deposition process. The method can be useful in the manufacture of semiconductor structures. The method includes: providing a substrate; providing a vapor including at least one compound of the formula (Formula I):

(Formula I):

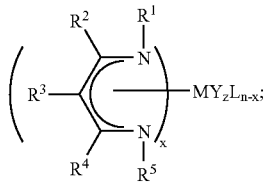

and contacting the vapor including the at least one compound of Formula I with the substrate (and typically directing the vapor to the substrate) to form a metal-containing layer on at least one surface of the substrate. The compound of the formula (Formula I) includes at least one β-diketiminate ligand, wherein M is selected from the group consisting of a Group 2 metal, a Group 3 metal, a Lanthanide, and combinations thereof; each L is independently an anionic ligand; each Y is independently a neutral ligand; n represents the valence state of the metal; z is from 0 to 10; x is from 1 to n; and each $R^1$, $R^2$, $R^3$, $R^4$, and $R^5$ is independently hydrogen or an organic group with the proviso that at least one of the R groups is a fluorine-containing organic group.

In another aspect, the present invention provides a method of forming a metal-containing layer on a substrate (e.g., a semiconductor substrate or substrate assembly) using a vapor deposition process. The method can be useful in the manufacture of semiconductor structures. The method includes: providing a substrate; providing a vapor including at least one compound of the formula (Formula I):

(Formula I):

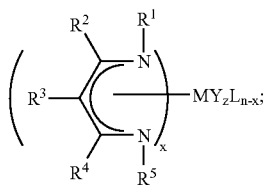

and contacting the vapor including the at least one compound of Formula I with the substrate (and typically directing the vapor to the substrate) to form a metal-containing layer on at least one surface of the substrate. The compound of the formula (Formula I) includes at least one β-diketiminate ligand, wherein M is selected from the group consisting of a Group 2 metal, a Group 3 metal, a Lanthanide, and combinations thereof; each L is independently an anionic ligand; each Y is independently a neutral ligand; n represents the valence state of the metal; z is from 0 to 10; x is from 1 to n; and each $R^1$, $R^2$, $R^3$, $R^4$, and $R^5$ is independently hydrogen or an aliphatic group (preferably an aliphatic moiety) having 1 to 5 carbon atoms, with the proviso that at least one of $R^2$, $R^3$, and $R^4$ is a moiety selected from the group consisting of ethyl, n-propyl, isopropyl, n-butyl, sec-butyl, isobutyl, n-pentyl, 2-pentyl, 3-pentyl, 2-methyl-1-butyl, 3-methyl-2-butyl, isopentyl, tert-pentyl, and neopentyl.

In another aspect, the present invention provides a method of forming a metal-containing layer on a substrate (e.g., a semiconductor substrate or substrate assembly) using a vapor deposition process. The method can be useful in the manufacture of semiconductor structures. The method includes: providing a substrate; providing a vapor including at least one compound of the formula (Formula I):

(Formula I):

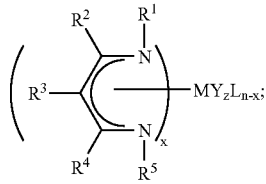

and contacting the vapor including the at least one compound of Formula I with the substrate (and typically directing the vapor to the substrate) to form a metal-containing layer on at least one surface of the substrate. The compound of the formula (Formula I) includes at least one β-diketiminate ligand, wherein M is selected from the group consisting of a Group 2 metal, a Group 3 metal, a Lanthanide, and combinations thereof; each L is independently an anionic ligand; each Y is independently a neutral ligand; n represents the valence state of the metal; z is from 0 to 10; x is from 1 to n; and each $R^1$, $R^2$, $R^3$, $R^4$, and $R^5$ is independently hydrogen or an aliphatic group (preferably an aliphatic moiety) having 1 to 5 carbon atoms, with the proviso that at least one of $R^1$ and $R^5$ is a moiety selected from the group consisting of n-propyl, n-butyl, sec-butyl, isobutyl, n-pentyl, 2-pentyl, 3-pentyl, 2-methyl-1-butyl, 3-methyl-2-butyl, isopentyl, and tert-pentyl.

In another aspect, the present invention provides metal-containing compounds having at least one β-diketiminate ligand, precursor compositions including such compounds, vapor deposition systems including such compounds, and methods of making such compounds. Such metal-containing compounds include those of the formula (Formula I):

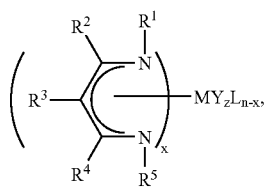

wherein: M is selected from the group consisting of a Group 2 metal, a Group 3 metal, a Lanthanide, and combinations thereof; each L is independently an anionic ligand; each Y is independently a neutral ligand; n represents the valence state of the metal; z is from 0 to 10; and x is from 1 to n; and each $R^1$, $R^2$, $R^3$, $R^4$, and $R^5$ is independently hydrogen or an organic group with the proviso that at least one of the R groups is a fluorine-containing organic group. The present invention also provides sources for β-diketiminate ligands having a fluorine-containing aliphatic group, and methods of making same, which are useful for making metal-containing compounds having at least one β-diketiminate ligand having a fluorine-containing organic group.

In another aspect, the present invention provides metal-containing compounds having certain β-diketiminate ligands, precursor compositions including such compounds, vapor deposition systems including such compounds, and methods of making such compounds. Such metal-containing compounds include those of the formula (Formula I):

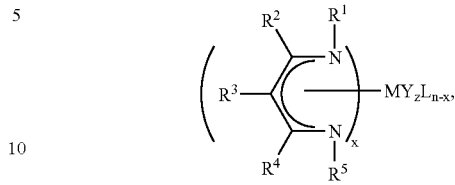

wherein: M is selected from the group consisting of a Group 2 metal, a Group 3 metal, a Lanthanide, and combinations thereof; each L is independently an anionic ligand; each Y is independently a neutral ligand; n represents the valence state of the metal; z is from 0 to 10; each $R^1$, $R^2$, $R^3$, $R^4$, and $R^5$ is independently hydrogen or an aliphatic group (preferably an aliphatic moiety) having 1 to 5 carbon atoms, with the proviso that at least one of $R^2$, $R^3$, and $R^4$ is a moiety selected from the group consisting of ethyl, n-propyl, isopropyl, n-butyl, sec-butyl, isobutyl, n-pentyl, 2-pentyl, 3-pentyl, 2-methyl-1-butyl, 3-methyl-2-butyl, isopentyl, tert-pentyl, and neopentyl.

In another aspect, the present invention provides metal-containing compounds having certain β-diketiminate ligands, precursor compositions including such compounds, vapor deposition systems including such compounds, and methods of making such compounds. Such metal-containing compounds include those of the formula (Formula I):

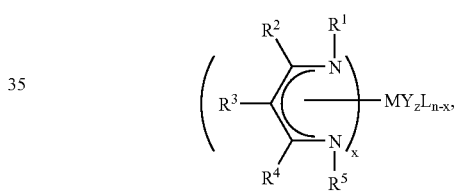

wherein: M is selected from the group consisting of a Group 2 metal, a Group 3 metal, a Lanthanide, and combinations thereof; each L is independently an anionic ligand; each Y is independently a neutral ligand; n represents the valence state of the metal; z is from 0 to 10; each $R^1$, $R^2$, $R^3$, $R^4$, and $R^5$ is independently hydrogen or an aliphatic group (preferably an aliphatic moiety) having 1 to 5 carbon atoms, with the proviso that at least one of $R^1$ and $R^5$ is a moiety selected from the group consisting of n-propyl, n-butyl, sec-butyl, isobutyl, n-pentyl, 2-pentyl, 3-pentyl, 2-methyl-1-butyl, 3-methyl-2-butyl, isopentyl, and tert-pentyl.

Advantageously, the metal-containing compounds of the present invention can have desirable properties (e.g., one or more of higher vapor pressure, lower melting point, and lower sublimation point) for use in vapor deposition methods.

Definitions

As used herein, formulas of the type:

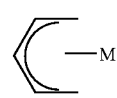

are used to represent pentadienyl-group type ligands (e.g., β-diketiminate ligands) having delocalized electron density that are coordinated to a metal. The ligands may be coordinated to the metal through one, two, three, four, and/or five atoms (i.e., $\eta^1$-, $\eta^2$-, $\eta^3$-, $\eta^4$-, and/or $\eta^5$-coordination modes).

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for metal-containing compounds of this invention are those that do not interfere with the formation of a metal oxide layer using vapor deposition techniques. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

As used herein, "metal-containing" is used to refer to a material, typically a compound or a layer, that may consist entirely of a metal, or may include other elements in addition to a metal. Typical metal-containing compounds include, but are not limited to, metals, metal-ligand complexes, metal salts, organometallic compounds, and combinations thereof. Typical metal-containing layers include, but are not limited to, metals, metal oxides, metal silicates, and combinations thereof.

As used herein, "a," "an," "the," and "at least one" are used interchangeably and mean one or more than one.

As used herein, the term "comprising," which is synonymous with "including" or "containing," is inclusive, open-ended, and does not exclude additional unrecited elements or method steps.

The terms "deposition process" and "vapor deposition process" as used herein refer to a process in which a metal-containing layer is formed on one or more surfaces of a substrate (e.g., a doped polysilicon wafer) from vaporized precursor composition(s) including one or more metal-containing compounds. Specifically, one or more metal-containing compounds are vaporized and directed to and/or contacted with one or more surfaces of a substrate (e.g., semiconductor substrate or substrate assembly) placed in a deposition chamber. Typically, the substrate is heated. These metal-containing compounds form (e.g., by reacting or decomposing) a non-volatile, thin, uniform, metal-containing layer on the surface(s) of the substrate. For the purposes of this invention, the term "vapor deposition process" is meant to include both chemical vapor deposition processes (including pulsed chemical vapor deposition processes) and atomic layer deposition processes.

"Chemical vapor deposition" (CVD) as used herein refers to a vapor deposition process wherein the desired layer is deposited on the substrate from vaporized metal-containing compounds (and any reaction gases used) within a deposition chamber with no effort made to separate the reaction components. In contrast to a "simple" CVD process that involves the substantial simultaneous use of the precursor compositions and any reaction gases, "pulsed" CVD alternately pulses these materials into the deposition chamber, but does not rigorously avoid intermixing of the precursor and reaction gas streams, as is typically done in atomic layer deposition or ALD (discussed in greater detail below).

The term "atomic layer deposition" (ALD) as used herein refers to a vapor deposition process in which deposition cycles, preferably a plurality of consecutive deposition cycles, are conducted in a process chamber (i.e., a deposition chamber). Typically, during each cycle the precursor is chemisorbed to a deposition surface (e.g., a substrate assembly surface or a previously deposited underlying surface such as material from a previous ALD cycle), forming a monolayer or sub-monolayer that does not readily react with additional precursor (i.e., a self-limiting reaction). Thereafter, if necessary, a reactant (e.g., another precursor or reaction gas) may subsequently be introduced into the process chamber for use in converting the chemisorbed precursor to the desired material on the deposition surface. Typically, this reactant is capable of further reaction with the precursor. Further, purging steps may also be utilized during each cycle to remove excess precursor from the process chamber and/or remove excess reactant and/or reaction byproducts from the process chamber after conversion of the chemisorbed precursor. Further, the term "atomic layer deposition," as used herein, is also meant to include processes designated by related terms such as, "chemical vapor atomic layer deposition"; "atomic layer epitaxy" (ALE) (see U.S. Pat. No. 5,256,244 to Ackerman), molecular beam epitaxy (MBE), gas source MBE, or organometallic MBE, and chemical beam epitaxy when performed with alternating pulses of precursor composition(s), reactive gas, and purge (e.g., inert carrier) gas.

As compared to the one cycle chemical vapor deposition (CVD) process, the longer duration multi-cycle ALD process allows for improved control of layer thickness and composition by self-limiting layer growth, and minimizing detrimental gas phase reactions by separation of the reaction components. The self-limiting nature of ALD provides a method of depositing a film on a wide variety of reactive surfaces, including surfaces with irregular topographies, with better step coverage than is available with CVD or other "line of sight" deposition methods such as evaporation or physical vapor deposition (PVD or sputtering).

DETAILED DESCRIPTION OF CERTAIN EMBODIMENTS

Figure 1:
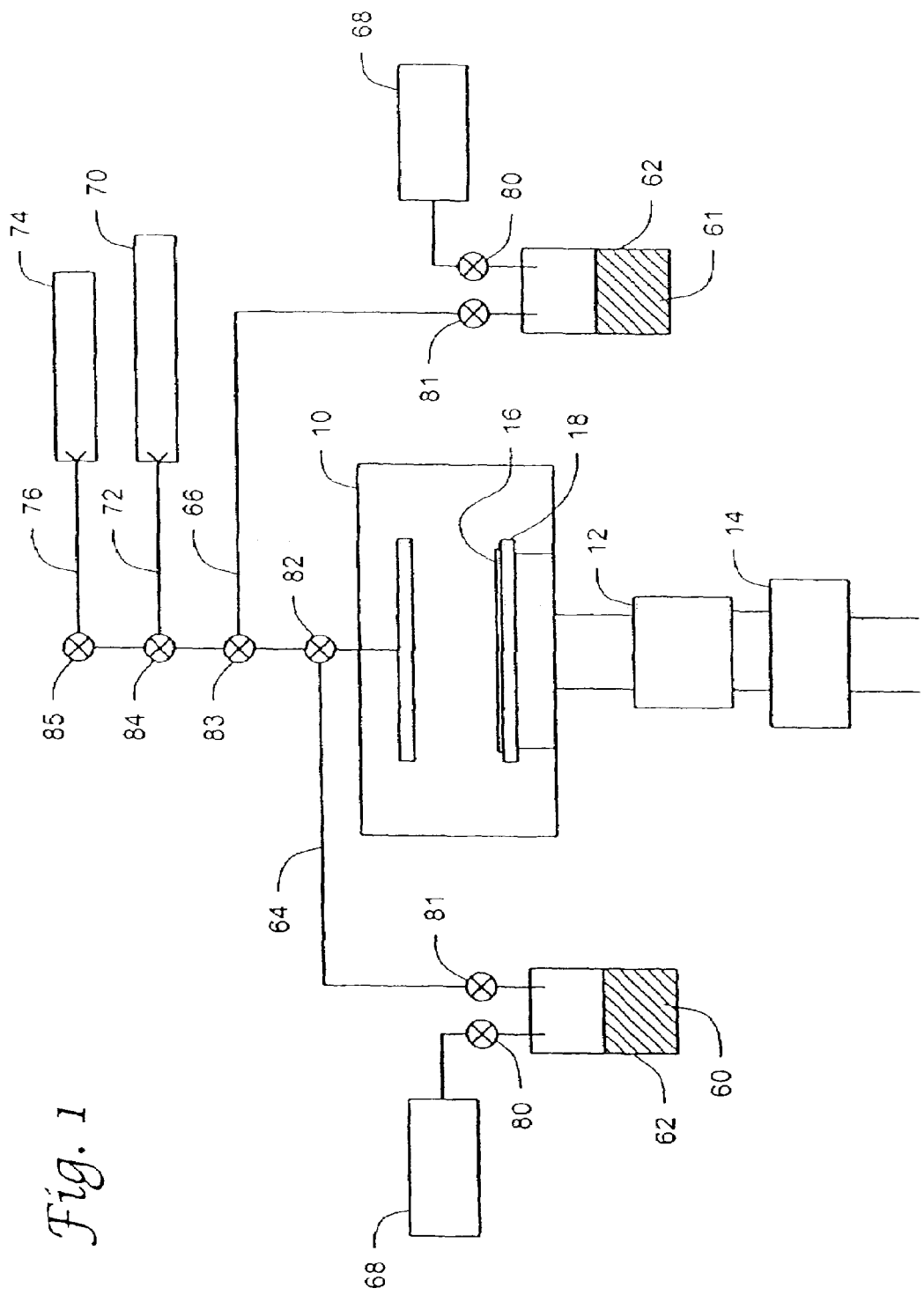
FIG. 1 is a perspective view of a vapor deposition system suitable for use in methods of the present invention.

Certain metal-containing compounds having at least one β-diketiminate ligand are known in the art. In such certain known metal-containing compounds, the β-diketiminate ligand has isopropyl substituents on both nitrogen atoms, or tert-butyl substituents on both nitrogen atoms. See, for example, El-Kaderi et al., *Organometallics*, 23:4995-5002 (2004). The present invention provides metal-containing compounds (i.e., metal-containing complexes) including at least one β-diketiminate ligand, which can have desirable properties (e.g., one or more of higher vapor pressure, lower melting point, and lower sublimation point) for use in vapor deposition methods. The present invention also provides methods of making and using such metal-containing compounds, and vapor deposition systems including the same.

In one aspect, the present invention provides metal-containing compounds having at least one β-diketiminate ligand with at least one fluorine-containing organic group as a substituent. Such metal-containing compounds including at least one fluorine-containing organic group can provide higher volatility than corresponding metal-containing compounds without a fluorine-containing organic group. Metal-containing compounds having higher volatility can be advantageous in deposition methods (e.g., CVD and ALD).

In another aspect, the present invention provides metal-containing compounds having at least one β-diketiminate ligand with at least one aliphatic group (preferably an aliphatic moiety) having 1 to 5 carbon atoms as a substituent, wherein the aliphatic group is selected to have greater degrees of freedom than the corresponding substituent in the β-diketiminate ligands of certain metal-containing compounds known in the art (i.e., compounds of Formula I wherein $R^2$=$R^4$=methyl; $R^3$=H; and $R^1$=$R^5$=isopropyl or $R^1$=$R^5$=tert-butyl). Such metal-containing compounds having at least one β-diketiminate ligand with at least one substituent having greater degrees of freedom than the corresponding substituent in certain known metal-containing compounds can have lower melting points and/or sublimation points than the certain known metal-containing compounds. Metal-containing compounds having lower melting points, lower sublimation points, or both, can be advantageous in deposition methods (e.g., CVD and ALD). For example, metal-containing compounds having lower melting points are particularly useful for molten precursor compositions, because the vapor pressure of molten materials is typically higher than that of analogous solid materials at the same temperature. In addition, the surface area of vaporizing molten precursor compositions (and thus the rates of vaporization from and heat transfer to such compositions) can change at regular and predictable rates. Finally, molten precursor compositions are typically not a source for undesirable particles in the deposition process. Thus, for a given class of precursor compositions, molten forms within that class can provide adequate vapor pressure for deposition at lower temperatures than non-molten forms, under reproducible conditions, and preferably without producing problematic particles in the process.

In some embodiments, the metal-containing compounds are homoleptic complexes (i.e., complexes in which the metal is bound to only one type of ligand) that include β-diketiminate ligands, which can be symmetric or unsymmetric. In other embodiments, the metal-containing compounds are heteroleptic complexes (i.e., complexes in which the metal is bound to more than one type of ligand) including at least one β-diketiminate ligand, which can be symmetric or unsymmetric. See, for example, copending U.S. application Ser. No. 11/169,082 (entitled "UNSYMMETRICAL LIGAND SOURCES, REDUCED SYMMETRY METAL-CONTAINING COMPOUNDS, AND SYSTEMS AND METHODS INCLUDING SAME," filed on the same day herewith. In some embodiments, the β-diketiminate ligand can be in the $\eta^5$-coordination mode.

Compounds with at Least One Fluorine-Containing Organic Group

In one aspect, metal-containing compounds including at least one β-diketiminate ligand having at least one fluorine-containing organic group, and precursor compositions including such compounds, are disclosed. Such metal-containing compounds including at least one fluorine-containing organic group can provide higher volatility than corresponding metal-containing compounds without a fluorine-containing organic group. Metal-containing compounds having higher volatility can be advantageous in deposition methods (e.g., CVD and ALD).

Such compounds include a compound of the formula (Formula I):

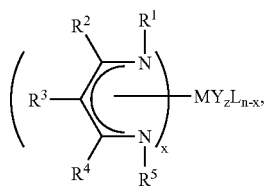

wherein M is a Group 2 metal (e.g., Ca, Sr, Ba), a Group 3 metal (e.g., Sc, Y, La), a Lanthanide (e.g., Pr, Nd), or a combination thereof. Preferably M is Ca, Sr, or Ba. More preferably M is Sr. Each L is independently an anionic ligand; each Y is independently a neutral ligand; n represents the valence state of the metal; z is from 0 to 10; and x is from 1 to n.

Each $R^1$, $R^2$, $R^3$, $R^4$, and $R^5$ is independently hydrogen or an organic group (e.g., an alkyl group or, in certain embodiments, an alkyl moiety), with the proviso that at least one R group is a fluorine-containing organic group. In certain embodiments, $R^1$, $R^2$, $R^3$, $R^4$, and $R^5$ are each independently hydrogen or an organic group having 1 to 10 carbon atoms (e.g., methyl, ethyl, propyl, isopropyl, butyl, sec-butyl, tert-butyl), and preferably hydrogen or an aliphatic group having 1 to 5 carbon atoms. In certain embodiments, $R^3$=H and at least one of $R^1$, $R^2$, $R^4$, and $R^5$ is a fluorine-containing organic group.

The fluorine-containing organic group may be a partially fluorinated group (i.e., some, but not all, of the hydrogens have been replaced by fluorine) or a fully fluorinated group (i.e., a perfluoro group in which all of the hydrogens have been replaced by fluorine). In certain embodiments, the fluorine-containing organic group is a fluorine-containing aliphatic group, and preferably a fluorine-containing alkyl group. Exemplary fluorine-containing alkyl groups include, —CH$_2$F, —CHF$_2$, —CF$_3$, —CH$_2$CF$_3$, —CF$_2$CF$_3$, —CH$_2$CH$_2$CF$_3$, —CF$_2$CF$_2$CF$_3$, —CH(CH$_3$)(CF$_3$), —CH(CF$_3$)$_2$, —CF(CF$_3$)$_2$, —CH$_2$CH$_2$CH$_2$CF$_3$, —CF$_2$CF$_2$CF$_2$CF$_3$, —CH(CF$_3$)(CF$_2$CF$_3$), —CF(CF$_3$)(CF$_2$CF$_3$), —C(CF$_3$)$_3$, and the like.

L can represent a wide variety of anionic ligands. Exemplary anionic ligands (L) include halides, alkoxide groups, amide groups, mercaptide groups, cyanide, alkyl groups, amidinate groups, guanidinate groups, isoureate groups, β-diketonate groups, β-iminoketonate groups, β-diketiminate groups, and combinations thereof. In certain embodiments, L is a β-diketiminate group having a structure that is the same as that of the β-diketiminate ligand shown in Formula I. In other certain embodiments, L is a β-diketiminate group (e.g., symmetric or unsymmetric) having a structure that is different than that of the β-diketiminate ligand shown in Formula I.

Y represents an optional neutral ligand. Exemplary neutral ligands (Y) include carbonyl (CO), nitrosyl (NO), ammonia (NH$_3$), amines (NR$_3$), nitrogen (N$_2$), phosphines (PR$_3$), ethers (ROR), alcohols (ROH), water (H$_2$O), tetrahydrofuran, and combinations thereof, wherein each R independently represents hydrogen or an organic group. The number of optional neutral ligands (Y) is represented by z, which is from 0 to 10, and preferably from 0 to 3. More preferably, Y is not present (i.e., z=0).

In one embodiment, a metal-containing compound including at least one β-diketiminate ligand having at least one fluorine-containing organic group as a substituent can be made, for example, by a method that includes combining components including a β-diketiminate ligand source having at least one fluorine-containing organic group as a substituent, a metal source, optionally a source for a neutral ligand Y, and a source for an anionic ligand L, which can be the same or different than the β-diketiminate ligand source having at least one fluorine-containing organic group as a substituent. Typically, a ligand source can be deprotonated to become a ligand.

An exemplary method includes combining components including: a ligand source of the formula (Formula III):

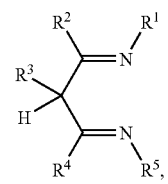

a tautomer thereof, or a deprotonated conjugate base or metal complex thereof (e.g., a tin complex); a source for an anionic ligand L (e.g., as described herein); optionally a source for a neutral ligand Y (e.g., as described herein); and a metal (M) source under conditions sufficient to form the metal-containing compound. Preferably, the components are combined in an organic solvent (e.g., heptane, toluene, or diethyl ether), typically under mixing or stirring conditions, and allowed to react at a convenient temperature (e.g., room temperature or below, refluxing or above, or an intermediate temperature) for a length of time to form a sufficient amount of the desired product. Preferably, the components are combined under an inert atmosphere (e.g., argon), typically in the substantial absence of water.

The metal (M) source can be selected from the group consisting of a Group II metal source, a Group III metal source, a Lanthanide metal source, and combinations thereof. A wide variety of suitable metal sources would be apparent to one of skill. Such metal sources can optionally include at least one neutral ligand Y as defined herein above. Exemplary metal sources include, for example, a M(II) halide (i.e., a M(II) compound having at least one halide ligand), a M(II) pseudohalide (i.e., a M(II) compound having at least one pseudohalide ligand), a M(II) amide (i.e., a M(II) compound having at least one amide ligand, e.g., a M(II) bis(hexamethyldisilazane) and/or a M(II) bis(hexamethyldisilazane)-bis(tetrahydrofuran)), a M(0) for use in a metal exchange reaction with a β-diketiminate metal complex (e.g., a tin complex), or combinations thereof.

Each $R^1$, $R^2$, $R^3$, $R^4$, and $R^5$ is independently hydrogen or an organic group (e.g., an alkyl group or, in certain embodiments, an alkyl moiety), with the proviso that at least one R group is a fluorine-containing organic group. In certain embodiments, $R^3$=H and at least one of $R^1$, $R^2$, $R^4$, and $R^5$ is a fluorine-containing organic group.

The method provides a metal-containing compound of the formula (Formula I):

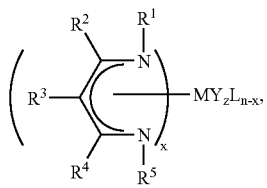

wherein M, L, Y, $R^1$, $R^2$, $R^3$, $R^4$, and $R^5$ are as defined above, n represents the valence state of the metal, z is from 0 to 10, and x is from 1 to n.

Sources for β-diketiminate ligands having at least one fluorine-containing aliphatic group as a substituent can be made, for example, using condensation reactions. For example, exemplary β-diketiminate ligand sources having at least one fluorine-containing aliphatic group can be made by a method including combining an amine of the formula $R^1NH_2$ with a compound of the formula (Formula IV):

(Formula IV):

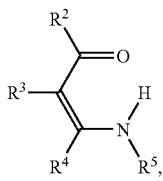

or a tautomer thereof, in the presence of an agent capable of activating the carbonyl group for reaction with the amine, under conditions sufficient to provide a ligand source of the formula (Formula III):

(Formula III):

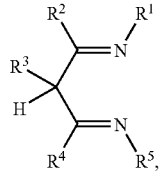

or a tautomer thereof.

Preferably, the components are combined in an organic solvent (e.g., heptane, toluene, or diethyl ether), typically under mixing or stirring conditions, and allowed to react at a convenient temperature (e.g., room temperature or below, refluxing or above, or an intermediate temperature) for a length of time to form a sufficient amount of the desired product. Preferably, the components are combined under an inert atmosphere (e.g., argon), typically in the substantial absence of water.

Each $R^1$, $R^2$, $R^3$, $R^4$, and $R^5$ is independently hydrogen or an aliphatic group (e.g., methyl, ethyl, propyl, isopropyl, butyl, sec-butyl, tert-butyl), with the proviso that at least one of the R groups is a fluorine-containing aliphatic group. In certain embodiments, $R^3$=H and at least one of $R^1$, $R^2$, $R^4$, and $R^5$ is a fluorine-containing aliphatic group. Accordingly, the present invention also provides ligand sources of Formula III.

Tautomers of compounds of Formula III and Formula IV include isomers in which a hydrogen atom is bonded to another atom. Typically, tautomers can be in equilibrium with one another.

Specifically, the present invention contemplates tautomers of Formula III including, for example,

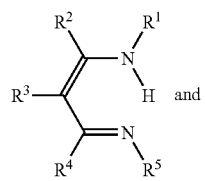 and 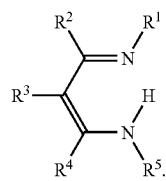

Similarly, the present invention contemplates tautomers of Formula IV including, for example,

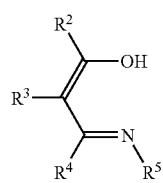 and 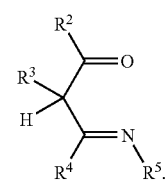

Suitable activating agents capable of activating a carbonyl group for reaction with an amine are well known to those of skill in the art and include, for example, alkylating agents and Lewis acids (e.g., $TiCl_4$). Exemplary alkylating agents include triethyloxonium tetrafluoroborate, dimethyl sulfate, nitrosoureas, mustard gases (e.g., 1,1-thiobis(2-chloroethane)), and combinations thereof.

Additional metal-containing compounds including at least one β-diketiminate ligand having at least one fluorine-containing organic group can be made, for example, by ligand exchange reactions between a metal-containing compound including at least one β-diketiminate ligand having at least one fluorine-containing organic group, and a metal-containing compound including at least one different β-diketiminate ligand. Such an exemplary method includes combining components including a compound of the formula (Formula I):

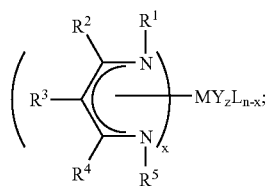

and a compound of the formula (Formula V):

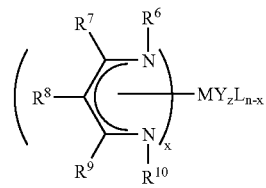

under conditions sufficient to form the metal-containing compound.

Each M is a Group 2 metal, a Group 3 metal, a Lanthanide, or a combination thereof; each L is independently an anionic ligand; each Y is independently a neutral ligand; n represents the valence state of the metal; z is from 0 to 10; and x is from 1 to n.

Each $R^1$, $R^2$, $R^3$, $R^4$, $R^5$, $R^6$, $R^7$, $R^8$, $R^9$, and $R^{10}$ is independently hydrogen or an organic group, with the proviso that at least one R group is a fluorine-containing organic group; and the β-diketiminate ligands shown in Formula I and Formula V have different structures.

The method can provide a metal-containing compound of the formula (Formula II):

(Formula II):

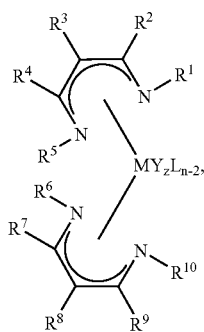

wherein M, L, Y, $R^1$, $R^2$, $R^3$, $R^4$, $R^5$, $R^6$, $R^7$, $R^8$, $R^9$, $R^{10}$, n, and z are as defined above.

Compounds with at Least One Substituent Having Greater Degrees of Freedom

In another aspect, the present invention provides metal containing compounds having at least one β-diketiminate ligand with at least one aliphatic group (preferably an aliphatic moiety) having 1 to 5 carbon atoms as a substituent, wherein the aliphatic group is selected to have greater degrees of freedom than the corresponding substituent in the β-diketiminate ligands of certain metal-containing compounds known in the art (i.e., compounds of Formula I wherein $R^2$=$R^4$ methyl; $R^3$=H; and $R^1$=$R^5$=isopropyl or $R^1$=$R^5$=tert-butyl). See, for example, El-Kaderi et al., *Organometallics*, 23:4995-5002 (2004).

One scheme for quantifying degrees of freedom of a substituent of a ligand of a metal-containing compound has been disclosed by Li et al. in *Inorganic Chemistry*, 44:1728-1735 (2005). In this scheme for counting the degrees of freedom, rotations about non-hydrogen single bonds (including the single bond attaching a substituent to a ligand) are counted. However, a single bond that only rotates a methyl group around its 3-fold axis, or a single bond that only rotates a tert-butyl group around its 3-fold axis, are ignored, because the resulting changes in energy might not have much influence on crystal packing. A chiral carbon atom (i.e., a carbon atom having four different substituents) counts as an additional degree of freedom, because enantiomers cannot interconvert at typical temperatures encountered in deposition methods. The above scheme was used to quantify degrees of freedom for some exemplary substituents, and the results are given in Table 1.

TABLE 1

| Total Degrees of Freedom Quantified for Exemplary Substituents | | | |
|---|---|---|---|
| Substituent | C—C Bond Rotations | Chiral Carbons | Degrees of Freedom |
| —H | 0 | 0 | 0 |
| —CH$_3$ (methyl) | 0 | 0 | 0 |
| —CH$_2$CH$_3$ (ethyl) | 1 | 0 | 1 |

TABLE 1-continued

| Total Degrees of Freedom Quantified for Exemplary Substituents | | | |
|---|---|---|---|
| Substituent | C—C Bond Rotations | Chiral Carbons | Degrees of Freedom |
| —CH$_2$CH$_2$CH$_3$ (n-propyl) | 2 | 0 | 2 |
| —CH(CH$_3$)$_2$ (isopropyl) | 1 | 0 | 1 |
| —CH$_2$CH$_2$CH$_2$CH$_3$ (n-butyl) | 3 | 0 | 3 |
| —CH(CH$_3$)(CH$_2$CH$_3$) (sec-butyl) | 2 | 1 | 3 |
| —CH$_2$CH(CH$_3$)$_2$ (isobutyl) | 2 | 0 | 2 |
| —C(CH$_3$)$_3$ (tert-butyl) | 0 | 0 | 0 |
| —CH$_2$CH$_2$CH$_2$CH$_2$CH$_3$ (n-pentyl) | 4 | 0 | 4 |
| —CH(CH$_3$)(CH$_2$CH$_2$CH$_3$) (2-pentyl) | 3 | 1 | 4 |
| —CH(CH$_2$CH$_3$)$_2$ (3-pentyl) | 3 | 0 | 3 |
| —CH$_2$CH(CH$_3$)(CH$_2$CH$_3$) (2-methyl-1-butyl) | 3 | 1 | 4 |
| —CH(CH$_3$)(CH(CH$_3$)$_2$) (3-methyl-2-butyl) | 2 | 1 | 3 |
| —CH$_2$CH$_2$CH(CH$_3$)$_2$ (isopentyl) | 3 | 0 | 3 |
| —C(CH$_3$)$_2$(CH$_2$CH$_3$) (tert-pentyl) | 2 | 0 | 2 |
| —CH$_2$C(CH$_3$)$_3$ (neopentyl) | 1 | 0 | 1 |

The above described method for quantifying degrees of freedom of a substituent of a ligand of a metal-containing compound is one exemplary approach. One of skill in the art will appreciate that other methods for quantifying degrees of freedom of a substituent of a ligand of a metal-containing compound could also be used as desired.

Such metal-containing compounds having at least one β-diketiminate ligand with at least one substituent having greater degrees of freedom than the corresponding substituent in certain known metal-containing compounds can have lower melting points and/or sublimation points than certain known metal-containing compounds with at least one β-diketiminate ligand. Metal-containing compounds having lower melting points, lower sublimation points, or both, can be advantageous in deposition methods (e.g., CVD and ALD). For example, metal-containing compounds having lower melting points are particularly useful for molten precursor compositions, because the vapor pressure of molten materials is typically higher than that of analogous solid materials at the same temperature. In addition, the surface area of vaporizing molten precursor compositions (and thus the rates of vaporization from and heat transfer to such compositions) can change at regular and predictable rates. Finally, molten precursor compositions are typically not a source for undesirable particles in the deposition process. Thus, for a given class of precursor compositions, molten forms within that class can provide adequate vapor pressure for deposition at lower temperatures than non-molten forms, under reproducible conditions, and preferably without producing problematic particles in the process.

In one aspect, the present invention provides metal-containing compounds having at least one β-diketiminate ligand with at least one substituent having greater degrees of freedom than the corresponding substituent in certain known metal-containing compounds. Such compounds include a compound of the formula (Formula I):

(Formula I):

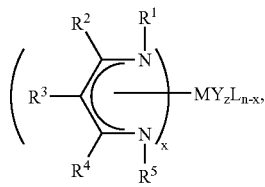

wherein M is a Group 2 metal (e.g., Ca, Sr, Ba), a Group 3 metal (e.g., Sc, Y, La), a Lanthanide (e.g., Pr, Nd), or a combination thereof. Preferably M is Ca, Sr, or Ba. More preferably, M is Sr. Each L is independently an anionic ligand; each Y is independently a neutral ligand; n represents the valence state of the metal; z is from 0 to 10; and x is from 1 to n.

In one embodiment, each $R^1$, $R^2$, $R^3$, $R^4$, and $R^5$ is independently hydrogen or an aliphatic group (e.g., an alkyl group or, in certain embodiments, an alkyl moiety) having 1 to 5 carbon atoms, with the proviso that at least one of $R^2$, $R^3$, and $R^4$ is a moiety selected from the group consisting of ethyl, n-propyl, isopropyl, n-butyl, sec-butyl, isobutyl, n-pentyl, 2-pentyl, 3-pentyl, 2-methyl-1-butyl, 3-methyl-2-butyl, isopentyl, tert-pentyl, and neopentyl. Notably the moieties listed in the above group all have higher quantified degrees of freedom (e.g., Table 1) than the corresponding substituents ($R^2$=$R^4$=methyl; and $R^3$=H) in the metal-containing compounds disclosed in El-Kaderi et al., *Organometallics*, 23:4995-5002 (2004).

In another embodiment, each $R^1$, $R^2$, $R^3$, $R^4$, and $R^5$ is independently hydrogen or an aliphatic group (e.g., an alkyl group or, in certain embodiments, an alkyl moiety) having 1 to 5 carbon atoms, with the proviso that at least one of $R^1$ and $R^5$ is a moiety selected from the group consisting of n-propyl, n-butyl, sec-butyl, isobutyl, n-pentyl, 2-pentyl, 3-pentyl, 2-methyl-1-butyl, 3-methyl-2-butyl, isopentyl, and tert-pentyl. Notably the moieties listed in the above group all have higher quantified degrees of freedom (e.g., Table 1) than the corresponding substituents ($R^1$=$R^5$=isopropyl; or $R^1$=$R^5$=tert-butyl) in the metal-containing compounds disclosed in El-Kaderi et al., *Organometallics*, 23:4995-5002 (2004).

L can represent a wide variety of anionic ligands. Exemplary anionic ligands (L) include halides, alkoxide groups, amide groups, mercaptide groups, cyanide, alkyl groups, amidinate groups, guanidinate groups, isoureate groups, β-diketonate groups, β-iminoketonate groups, β-diketiminate groups, and combinations thereof. In certain embodiments, L is a β-diketiminate group having a structure that is the same as that of the β-diketiminate ligand shown in Formula I. In other certain embodiments, L is a β-diketiminate group (e.g., symmetric or unsymmetric) having a structure that is different than that of the β-diketiminate ligand shown in Formula I.

Y represents an optional neutral ligand. Exemplary neutral ligands (Y) include carbonyl (CO), nitrosyl (NO), ammonia ($NH_3$), amines ($NR_3$), nitrogen ($N_2$), phosphines ($PR_3$), ethers (ROR), alcohols (ROH), water ($H_2O$), tetrahydrofuran, and combinations thereof, wherein each R independently represents hydrogen or an organic group. The number of optional neutral ligands (Y) is represented by z, which is from 0 to 10, and preferably from 0 to 3. More preferably, Y is not present (i.e., z=0).

In one embodiment, a metal-containing compound including at least one β-diketiminate ligand with at least one substituent having greater degrees of freedom than the corresponding substituent in certain known metal-containing compounds can be made, for example, by a method that includes combining components including a β-diketiminate ligand source with at least one substituent having greater degrees of freedom than the corresponding substituent in certain known metal-containing compounds, a metal source, optionally a source for a neutral ligand Y, and a source for an anionic ligand L, which can be the same or different than the β-diketiminate ligand source with at least one substituent having greater degrees of freedom than the corresponding substituent in certain known metal-containing compounds. Typically, a ligand source can be deprotonated to become a ligand.

An exemplary method includes combining components including: a ligand source of the formula (Formula III):

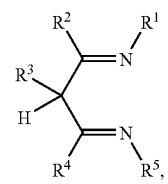

a tautomer thereof, or a deprotonated conjugate base or metal complex thereof; a source for an anionic ligand L (e.g., as described herein); optionally a source for a neutral ligand Y (e.g., as described herein); and a metal (M) source under conditions sufficient to form the metal-containing compound. Preferably, the components are combined in an organic solvent (e.g., heptane, toluene, or diethyl ether), typically under mixing or stirring conditions, and allowed to react at a convenient temperature (e.g., room temperature or below, refluxing or above, or an intermediate temperature) for a length of time to form a sufficient amount of the desired product. Preferably, the components are combined under an inert atmosphere (e.g., argon), typically in the substantial absence of water.

The metal (M) source can be selected from the group consisting of a Group II metal source, a Group III metal source, a Lanthanide metal source, and combinations thereof. A wide variety of suitable metal sources would be apparent to one of skill. Such metal sources can optionally include at least one neutral ligand Y as defined herein above. Exemplary metal sources include, for example, a M(II) halide (i.e., a M(II) compound having at least one halide ligand), a M(II) pseudohalide (i.e., a M(II) compound having at least one pseudohalide ligand), a M(II) amide (i.e., a M(II) compound having at least one amide ligand, e.g., a M(II) bis(hexamethyldisilazane) and/or a M(II) bis(hexamethyldisilazane)-bis(tetrahydrofuran)), a M(O) for use in a metal exchange reaction with a β-diketiminate metal complex (e.g., a tin complex), or combinations thereof.

In one embodiment, each $R^1$, $R^2$, $R^3$, $R^4$, and $R^5$ is independently hydrogen or an aliphatic group (e.g., an alkyl group or, in certain embodiments, an alkyl moiety) having 1 to 5 carbon atoms, with the proviso that at least one of $R^2$, $R^3$, and $R^4$ is a moiety selected from the group consisting of ethyl, n-propyl, isopropyl, n-butyl, sec-butyl, isobutyl, n-pentyl, 2-pentyl, 3-pentyl, 2-methyl-1-butyl, 3-methyl-2-butyl, isopentyl, tert-pentyl, and neopentyl.

In another embodiment, each $R^1$, $R^2$, $R^3$, $R^4$, and $R^5$ is independently hydrogen or an aliphatic group (e.g., an alkyl group or, in certain embodiments, an alkyl moiety) having 1 to 5 carbon atoms, with the proviso that at least one of $R^1$ and $R^5$ is a moiety selected from the group consisting of n-propyl, n-butyl, sec-butyl, isobutyl, n-pentyl, 2-pentyl, 3-pentyl, 2-methyl-1-butyl, 3-methyl-2-butyl, isopentyl, and tert-pentyl.

The method provides a metal-containing compound of the formula (Formula I):

(Formula I):

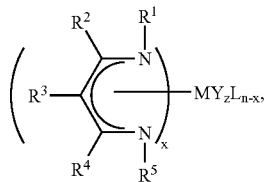

wherein M, L, Y, $R^1$, $R^2$, $R^3$, $R^4$, and $R^5$ are as defined above, n represents the valence state of the metal, z is from 0 to 10, and x is from 1 to n.

Sources for β-diketiminate ligands having at least one substituent having greater degrees of freedom than the corresponding substituent in certain known metal-containing compounds can be made, for example, using condensation reactions. For example, exemplary β-diketiminate ligand sources having at least one substituent having greater degrees of freedom than the corresponding substituent in certain known metal-containing compounds can be made by a method including combining an amine of the formula $R^1NH_2$ with a compound of the formula (Formula IV):

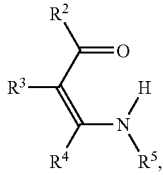

or a tautomer thereof, in the presence of an agent capable of activating the carbonyl group for reaction with the amine, under conditions sufficient to provide a ligand source of the formula (Formula III):

(Formula III):

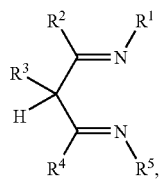

or a tautomer thereof. Preferably, the components are combined in an organic solvent (e.g., heptane, toluene, or diethyl ether), typically under mixing or stirring conditions, and allowed to react at a convenient temperature (e.g., room temperature or below, refluxing or above, or an intermediate temperature) for a length of time to form a sufficient amount of the desired product. Preferably, the components are combined under an inert atmosphere (e.g., argon), typically in the substantial absence of water.

In one embodiment, each $R^1$, $R^2$, $R^3$, $R^4$, and $R^5$ is independently hydrogen or an aliphatic group (e.g., an alkyl group or, in certain embodiments, an alkyl moiety) having 1 to 5 carbon atoms, with the proviso that at least one of $R^2$, $R^3$, and $R^4$ is a moiety selected from the group consisting of ethyl, n-propyl, isopropyl, n-butyl, sec-butyl, isobutyl, n-pentyl, 2-pentyl, 3-pentyl, 2-methyl-1-butyl, 3-methyl-2-butyl, isopentyl, tert-pentyl, and neopentyl.

In another embodiment, each $R^1$, $R^2$, $R^3$, $R^4$, and $R^5$ is independently hydrogen or an aliphatic group (e.g., an alkyl group or, in certain embodiments, an alkyl moiety) having 1 to 5 carbon atoms, with the proviso that at least one of $R^1$ and $R^5$ is a moiety selected from the group consisting of n-propyl, n-butyl, sec-butyl, isobutyl, n-pentyl, 2-pentyl, 3-pentyl, 2-methyl-1-butyl, 3-methyl-2-butyl, isopentyl, and tert-pentyl.

Tautomers of compounds of Formula III and Formula IV include isomers in which a hydrogen atom is bonded to another atom. Typically, tautomers can be in equilibrium with one another.

Specifically, the present invention contemplates tautomers of Formula III including, for example,

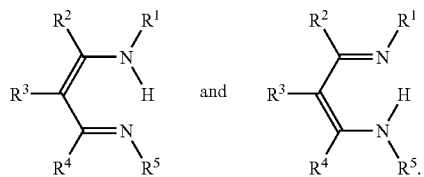

Similarly, the present invention contemplates tautomers of Formula IV including, for example,

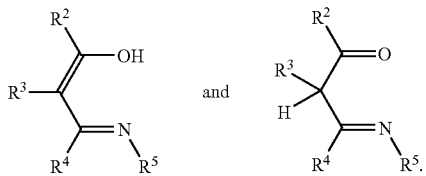

Suitable activating agents capable of activating a carbonyl group for reaction with an amine are well known to those of skill in the art and include, for example, alkylating agents and Lewis acids (e.g., $TiCl_4$). Exemplary alkylating agents include triethyloxonium tetrafluoroborate, dimethyl sulfate, nitrosoureas, mustard gases (e.g., 1,1-thiobis(2-chloroethane)), and combinations thereof.

Additional metal-containing compounds including at least one β-diketiminate ligand having at least one substituent having greater degrees of freedom than the corresponding substituent in certain known metal-containing compounds can be made, for example, by ligand exchange reactions between a metal-containing compound including at least one β-diketiminate ligand having at least one substituent having greater degrees of freedom than the corresponding substituent in certain known metal-containing compounds, and a metal-containing compound including at least one different β-diketiminate ligand. Such an exemplary method includes combining components including a compound of the formula (Formula I):

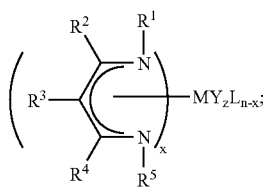

and a compound of the formula (Formula V):

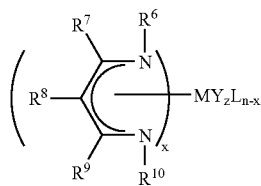

under conditions sufficient to form the metal-containing compound.

Each M is a Group 2 metal, a Group 3 metal, a Lanthanide, or a combination thereof; each L is independently an anionic ligand; each Y is independently a neutral ligand; n represents the valence state of the metal; z is from 0 to 10; and x is from 1 to n.

In one embodiment, each $R^1$, $R^2$, $R^3$, $R^4$, $R^5$, $R^6$, $R^7$, $R^8$, $R^9$, and $R^{10}$ is independently hydrogen or an aliphatic group (e.g., an alkyl group or, in certain embodiments, an alkyl moiety) having 1 to 5 carbon atoms, with the proviso that at least one of $R^2$, $R^3$, $R^4$, $R^7$, $R^8$, and $R^9$ is a moiety selected from the group consisting of ethyl, n-propyl, isopropyl, n-butyl, sec-butyl, isobutyl, n-pentyl, 2-pentyl, 3-pentyl, 2-methyl-1-butyl, 3-methyl-2-butyl, isopentyl, tert-pentyl, and neopentyl; and the α-diketiminate ligands shown in Formula I and Formula V have different structures.

In another embodiment, each $R^1$, $R^2$, $R^3$, $R^4$, $R^5$, $R^6$, $R^7$, $R^8$, $R^9$, and $R^{10}$ is independently hydrogen or an aliphatic group (e.g., an alkyl group or, in certain embodiments, an alkyl moiety) having 1 to 5 carbon atoms, with the proviso that at least one of $R^1$, $R^5$, $R^6$, and $R^{10}$ is a moiety selected from the group consisting of n-propyl, n-butyl, sec-butyl, isobutyl, n-pentyl, 2-pentyl, 3-pentyl, 2-methyl-1-butyl, 3-methyl-2-butyl, isopentyl, and tert-pentyl; and the β-diketiminate ligands shown in Formula I and Formula V have different structures.

The method can provide a metal-containing compound of the formula (Formula II):

(Formula II):

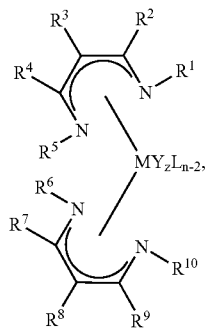

wherein M, L, Y, $R^1$, $R^2$, $R^3$, $R^4$, $R^5$, $R^6$, $R^7$, $R^8$, $R^9$, $R^{10}$, n, and z are as defined above.

Other Metal-Containing Compounds

Precursor compositions that include a metal-containing compound that includes at least one β-diketiminate ligand can be useful for depositing metal-containing layers using vapor deposition methods. In addition, such vapor deposition methods can also include precursor compositions that include one or more different metal-containing compounds. Such precursor compositions can be deposited/chemisorbed, for example in an ALD process discussed more fully below, substantially simultaneously with or sequentially to, the precursor compositions including metal-containing compounds with at least one β-diketiminate ligand. The metals of such different metal-containing compounds can include, for example, Ti, Ta, Bi, Hf, Zr, Pb, Nb, Mg, Al, and combinations thereof. Suitable different metal-containing compounds include, for example, tetrakis titanium isopropoxide, titanium tetrachloride, trichlorotitanium dialkylamides, tetrakis titanium dialkylamides, tetrakis hafnium dialkylamides, trimethyl aluminum, zirconium (IV) chloride, pentakis tantalum ethoxide, and combinations thereof.

Vapor Deposition Methods

The metal-containing layer can be deposited, for example, on a substrate (e.g., a semiconductor substrate or substrate assembly). "Semiconductor substrate" or "substrate assembly" as used herein refer to a semiconductor substrate such as a base semiconductor layer or a semiconductor substrate having one or more layers, structures, or regions formed thereon. A base semiconductor layer is typically the lowest layer of silicon material on a wafer or a silicon layer deposited on another material, such as silicon on sapphire. When reference is made to a substrate assembly, various process steps may have been previously used to form or define regions, junctions, various structures or features, and openings such as transistors, active areas, diffusions, implanted regions, vias, contact openings, high aspect ratio openings, capacitor plates, barriers for capacitors, etc.

"Layer," as used herein, refers to any layer that can be formed on a substrate from one or more precursors and/or reactants according to the deposition process described herein. The term "layer" is meant to include layers specific to the semiconductor industry, such as, but clearly not limited to, a barrier layer, dielectric layer (i.e., a layer having a high dielectric constant), and conductive layer. The term "layer" is synonymous with the term "film" frequently used in the semiconductor industry. The term "layer" is also meant to include layers found in technology outside of semiconductor technology, such as coatings on glass. For example, such layers can be formed directly on fibers, wires, etc., which are substrates other than semiconductor substrates. Further, the layers can be formed directly on the lowest semiconductor surface of the substrate, or they can be formed on any of a variety of layers (e.g., surfaces) as in, for example, a patterned wafer.

The layers or films formed may be in the form of metal-containing films, such as reduced metals, metal silicates, metal oxides, metal nitrides, etc, as well as combinations thereof. For example, a metal oxide layer may include a single metal, the metal oxide layer may include two or more different metals (i.e., it is a mixed metal oxide), or a metal oxide layer may optionally be doped with other metals.

If the metal oxide layer includes two or more different metals, the metal oxide layer can be in the form of alloys, solid solutions, or nanolaminates. Preferably, these have dielectric properties. The metal oxide layer (particularly if it is a dielectric layer) preferably includes one or more of $BaTiO_3$, $SrTiO_3$, $CaTiO_3$, $(Ba,Sr)TiO_3$, $SrTa_2O_6$, $SrBi_2Ta_2O_9$ (SBT), $SrHfO_3$, $SrZrO_3$, $BaHfO_3$, $BaZrO_3$, $(Pb,Ba)Nb_2O_6$, $(Sr,Ba)Nb_2O_6$, $Pb[(Sc,Nb)_{0.575}Ti_{0.425}]O_3$ (PSNT), $La_2O_3$, $Y_2O_3$, $LaAlO_3$, $YAlO_3$, $Pr_2O_3$, $Ba(Li,Nb)_{1/4}O_3$—$PbTiO_3$, and $Ba(0.6)Sr(0.4)TiO_3$—$MgO$. Surprisingly, the metal oxide layer formed according to the present invention is essentially free of carbon. Preferably metal-oxide layers formed by the systems and methods of the present invention are essentially free of carbon, hydrogen, halides, phosphorus, sulfur, nitrogen or compounds thereof. As used herein, "essentially free" is defined to mean that the metal-containing layer may include a small amount of the above impurities. For example, for metal-oxide layers, "essentially free" means that the above impurities are present in an amount of less than 1 atomic percent, such that they have a minor effect on the chemical properties, mechanical properties, physical form (e.g., crystallinity), or electrical properties of the film.

Various metal-containing compounds can be used in various combinations, optionally with one or more organic solvents (particularly for CVD processes), to form a precursor composition. Advantageously, some of the metal-containing compounds disclosed herein can be used in ALD without adding solvents. "Precursor" and "precursor composition" as used herein, refer to a composition usable for forming, either alone or with other precursor compositions (or reactants), a layer on a substrate assembly in a deposition process. Further, one skilled in the art will recognize that the type and amount of precursor used will depend on the content of a layer which is ultimately to be formed using a vapor deposition process. The preferred precursor compositions of the present invention are preferably liquid at the vaporization temperature and, more preferably, are preferably liquid at room temperature.

The precursor compositions may be liquids or solids at room temperature (preferably, they are liquids at the vaporization temperature). Typically, they are liquids sufficiently volatile to be employed using known vapor deposition techniques. However, as solids they may also be sufficiently volatile that they can be vaporized or sublimed from the solid state using known vapor deposition techniques. If they are less volatile solids, they are preferably sufficiently soluble in an organic solvent or have melting points below their decomposition temperatures such that they can be used in flash vaporization, bubbling, microdroplet formation techniques, etc.

Herein, vaporized metal-containing compounds may be used either alone or optionally with vaporized molecules of other metal-containing compounds or optionally with vaporized solvent molecules or inert gas molecules, if used. As used herein, "liquid" refers to a solution or a neat liquid (a liquid at room temperature or a solid at room temperature that melts at an elevated temperature). As used herein, "solution" does not require complete solubility of the solid but may allow for some undissolved solid, as long as there is a sufficient amount of the solid delivered by the organic solvent into the vapor phase for chemical vapor deposition processing. If solvent dilution is used in deposition, the total molar concentration of solvent vapor generated may also be considered as a inert carrier gas.

"Inert gas" or "non-reactive gas," as used herein, is any gas that is generally unreactive with the components it comes in contact with. For example, inert gases are typically selected from a group including nitrogen, argon, helium, neon, krypton, xenon, any other non-reactive gas, and mixtures thereof. Such inert gases are generally used in one or more purging processes described according to the present invention, and in some embodiments may also be used to assist in precursor vapor transport.

Solvents that are suitable for certain embodiments of the present invention may be one or more of the following: aliphatic hydrocarbons or unsaturated hydrocarbons (C3-C20, and preferably C5-C10, cyclic, branched, or linear), aromatic hydrocarbons (C5-C20, and preferably C5-C10), halogenated hydrocarbons, silylated hydrocarbons such as alkylsilanes, alkylsilicates, ethers, polyethers, thioethers, esters, lactones, nitrites, silicone oils, or compounds containing combinations of any of the above or mixtures of one or more of the above. The compounds are also generally compatible with each other, so that mixtures of variable quantities of the metal-containing compounds will not interact to significantly change their physical properties.

The precursor compositions of the present invention can, optionally, be vaporized and deposited/chemisorbed substantially simultaneously with, and in the presence of, one or more reaction gases. Alternatively, the metal-containing layers may be formed by alternately introducing the precursor composition and the reaction gas(es) during each deposition cycle. Such reaction gases may typically include oxygen, water vapor, ozone, nitrogen oxides, sulfur oxides, hydrogen, hydrogen sulfide, hydrogen selenide, hydrogen telluride, hydrogen peroxide, ammonia, organic amines, hydrazines (e.g., hydrazine, methylhydrazine, symmetrical and unsymmetrical dimethylhydrazines), silanes, disilanes and higher silanes, diborane, plasma, air, borazene (nitrogen source), carbon monoxide (reductant), alcohols, and any combination of these gases. For example, oxygen-containing sources are typically used for the deposition of metal-oxide layers. Preferable optional reaction gases used in the formation of metal-oxide layers include oxidizing gases (e.g., oxygen, ozone, and nitric oxide).

Suitable substrate materials of the present invention include conductive materials, semiconductive materials, conductive metal-nitrides, conductive metals, conductive metal oxides, etc. The substrate on which the metal-containing layer is formed is preferably a semiconductor substrate or substrate assembly. A wide variety of semiconductor materials are contemplated, such as for example, borophosphosilicate glass (BPSG), silicon such as, e.g., conductively doped polysilicon, monocrystalline silicon, etc. (for this invention, appropriate forms of silicon are simply referred to as "silicon"), for example in the form of a silicon wafer, tetraethylorthosilicate (TEOS) oxide, spin on glass (i.e., a thin layer of $SiO_2$, optionally doped, deposited by a spin on process), TiN, TaN, W, Ru, Al, Cu, noble metals, etc. A substrate assembly may also contain a layer that includes platinum, iridium, iridium oxide, rhodium, ruthenium, ruthenium oxide, strontium ruthenate, lanthanum nickelate, titanium nitride, tantalum nitride, tantalum-silicon-nitride, silicon dioxide, aluminum, gallium arsenide, glass, etc., and other existing or to-be-developed materials used in semiconductor constructions, such as dynamic random access memory (DRAM) devices, static random access memory (SRAM) devices, and ferroelectric memory (FERAM) devices, for example.

For substrates including semiconductor substrates or substrate assemblies, the layers can be formed directly on the lowest semiconductor surface of the substrate, or they can be formed on any of a variety of the layers (i.e., surfaces) as in a patterned wafer, for example.

Substrates other than semiconductor substrates or substrate assemblies can also be used in methods of the present invention. Any substrate that may advantageously form a metal-containing layer thereon, such as a metal oxide layer, may be used, such substrates including, for example, fibers, wires, etc.

A preferred deposition process for the present invention is a vapor deposition process. Vapor deposition processes are generally favored in the semiconductor industry due to the process capability to quickly provide highly conformal layers even within deep contacts and other openings.

The precursor compositions can be vaporized in the presence of an inert carrier gas if desired. Additionally, an inert carrier gas can be used in purging steps in an ALD process (discussed below). The inert carrier gas is typically one or more of nitrogen, helium, argon, etc. In the context of the present invention, an inert carrier gas is one that does not interfere with the formation of the metal-containing layer. Whether done in the presence of a inert carrier gas or not, the vaporization is preferably done in the absence of oxygen to avoid oxygen contamination of the layer (e.g., oxidation of silicon to form silicon dioxide or oxidation of precursor in the vapor phase prior to entry into the deposition chamber).

Chemical vapor deposition (CVD) and atomic layer deposition (ALD) are two vapor deposition processes often employed to form thin, continuous, uniform, metal-containing layers onto semiconductor substrates. Using either vapor deposition process, typically one or more precursor compositions are vaporized in a deposition chamber and optionally combined with one or more reaction gases and directed to and/or contacted with the substrate to form a metal-containing layer on the substrate. It will be readily apparent to one skilled in the art that the vapor deposition process may be enhanced by employing various related techniques such as plasma assistance, photo assistance, laser assistance, as well as other techniques.

Chemical vapor deposition (CVD) has been extensively used for the preparation of metal-containing layers, such as dielectric layers, in semiconductor processing because of its ability to provide conformal and high quality dielectric layers at relatively fast processing times. Typically, the desired precursor compositions are vaporized and then introduced into a deposition chamber containing a heated substrate with optional reaction gases and/or inert carrier gases in a single deposition cycle. In a typical CVD process, vaporized precursors are contacted with reaction gas(es) at the substrate surface to form a layer (e.g., dielectric layer). The single deposition cycle is allowed to continue until the desired thickness of the layer is achieved.

Typical CVD processes generally employ precursor compositions in vaporization chambers that are separated from the process chamber wherein the deposition surface or wafer is located. For example, liquid precursor compositions are typically placed in bubblers and heated to a temperature at which they vaporize, and the vaporized liquid precursor composition is then transported by an inert carrier gas passing over the bubbler or through the liquid precursor composition. The vapors are then swept through a gas line to the deposition chamber for depositing a layer on substrate surface(s) therein. Many techniques have been developed to precisely control this process. For example, the amount of precursor composition transported to the deposition chamber can be precisely controlled by the temperature of the reservoir containing the precursor composition and by the flow of an inert carrier gas bubbled through or passed over the reservoir.

A typical CVD process may be carried out in a chemical vapor deposition reactor, such as a deposition chamber available under the trade designation of 7000 from Genus, Inc. (Sunnyvale, Calif.), a deposition chamber available under the trade designation of 5000 from Applied Materials, Inc. (Santa Clara, Calif.), or a deposition chamber available under the trade designation of Prism from Novelus, Inc. (San Jose, Calif.). However, any deposition chamber suitable for performing CVD may be used.

Several modifications of the CVD process and chambers are possible, for example, using atmospheric pressure chemical vapor deposition, low pressure chemical vapor deposition (LPCVD), plasma enhanced chemical vapor deposition (PECVD), hot wall or cold wall reactors or any other chemical vapor deposition technique. Furthermore, pulsed CVD can be used, which is similar to ALD (discussed in greater detail below) but does not rigorously avoid intermixing of precursor and reactant gas streams. Also, for pulsed CVD, the deposition thickness is dependent on the exposure time, as opposed to ALD, which is self-limiting (discussed in more detail below).

Alternatively, and preferably, the vapor deposition process employed in the methods of the present invention is a multi-cycle atomic layer deposition (ALD) process. Such a process is advantageous, in particular advantageous over a CVD process, in that it provides for improved control of atomic-level thickness and uniformity to the deposited layer (e.g., dielectric layer) by providing a plurality of deposition cycles. The self-limiting nature of ALD provides a method of depositing a film on a wide variety of reactive surfaces including, for example, surfaces with irregular topographies, with better step coverage than is available with CVD or other "line of sight" deposition methods (e.g., evaporation and physical vapor deposition, i.e., PVD or sputtering). Further, ALD processes typically expose the metal-containing compounds to lower volatilization and reaction temperatures, which tends to decrease degradation of the precursor as compared to, for example, typical CVD processes. See, for example, copending U.S. application Ser. No. 11/168,160 (entitled "ATOMIC LAYER DEPOSITION SYSTEMS AND METHODS INCLUDING METAL BETA-DIKETIMINATE COMPOUNDS," on the same day herewith.

Generally, in an ALD process each reactant is pulsed sequentially onto a suitable substrate, typically at deposition temperatures of at least 25° C., preferably at least 150° C., and more preferably at least 200° C. Typical ALD deposition temperatures are no greater than 400° C., preferably no greater than 350° C., and even more preferably no greater than 250° C. These temperatures are generally lower than those presently used in CVD processes, which typically include deposition temperatures at the substrate surface of at least 150° C., preferably at least 200° C., and more preferably at least 250° C. Typical CVD deposition temperatures are no greater than 600° C., preferably no greater than 500° C., and even more preferably no greater than 400° C.

Under such conditions the film growth by ALD is typically self-limiting (i.e., when the reactive sites on a surface are used up in an ALD process, the deposition generally stops), insuring not only excellent conformality but also good large area uniformity plus simple and accurate composition and thickness control. Due to alternate dosing of the precursor compositions and/or reaction gases, detrimental vapor-phase reactions are inherently eliminated, in contrast to the CVD process that is carried out by continuous co-reaction of the precursors and/or reaction gases. (See Vehkamäki et al, "Growth of $SrTiO_3$ and $BaTiO_3$ Thin Films by Atomic Layer Deposition," Electrochemical and Solid-State Letters, 2(10): 504-506 (1999)).

A typical ALD process includes exposing a substrate (which may optionally be pretreated with, for example, water and/or ozone) to a first chemical to accomplish chemisorption of the species onto the substrate. The term "chemisorption" as used herein refers to the chemical adsorption of vaporized reactive metal-containing compounds on the surface of a substrate. The adsorbed species are typically irreversibly bound to the substrate surface as a result of relatively strong binding forces characterized by high adsorption energies (e.g., >30 kcal/mol), comparable in strength to ordinary chemical bonds. The chemisorbed species typically form a monolayer on the substrate surface. (See "The Condensed Chemical Dictionary", 10th edition, revised by G. G. Hawley, published by Van Nostrand Reinhold Co., New York, 225 (1981)). The technique of ALD is based on the principle of the formation of a saturated monolayer of reactive precursor molecules by chemisorption. In ALD one or more appropriate precursor compositions or reaction gases are alternately introduced (e.g., pulsed) into a deposition chamber and chemisorbed onto the surfaces of a substrate. Each sequential introduction of a reactive compound (e.g., one or more precursor compositions and one or more reaction gases) is typically separated by an inert carrier gas purge. Each precursor composition co-reaction adds a new atomic layer to previously deposited layers to form a cumulative solid layer. The cycle is repeated to gradually form the desired layer thickness. It should be understood that ALD can alternately utilize one precursor composition, which is chemisorbed, and one reaction gas, which reacts with the chemisorbed species.

Practically, chemisorption might not occur on all portions of the deposition surface (e.g., previously deposited ALD material). Nevertheless, such imperfect monolayer is still considered a monolayer in the context of the present invention. In many applications, merely a substantially saturated monolayer may be suitable. A substantially saturated monolayer is one that will still yield a deposited monolayer or less of material exhibiting the desired quality and/or properties.

A typical ALD process includes exposing an initial substrate to a first chemical species A (e.g., a metal-containing compound as described herein) to accomplish chemisorption of the species onto the substrate. Species A can react either with the substrate surface or with Species B (described below) but not with itself. Typically in chemisorption, one or more of the ligands of Species A is displaced by reactive groups on the substrate surface. Theoretically, the chemisorption forms a monolayer that is uniformly one atom or molecule thick on the entire exposed initial substrate, the monolayer being composed of Species A, less any displaced ligands. In other words, a saturated monolayer is substantially formed on the substrate surface. Practically, chemisorption may not occur on all portions of the substrate. Nevertheless, such a partial monolayer is still understood to be a monolayer in the context of the present invention. In many applications, merely a substantially saturated monolayer may be suitable. In one aspect, a substantially saturated monolayer is one that will still yield a deposited monolayer or less of material exhibiting the desired quality and/or properties. In another aspect, a substantially saturated monolayer is one that is self-limited to further reaction with precursor.

The first species (e.g., substantially all non-chemisorbed molecules of Species A) as well as displaced ligands are purged from over the substrate and a second chemical species, Species B (e.g., a different metal-containing compound or reactant gas) is provided to react with the monolayer of Species A. Species B typically displaces the remaining ligands from the Species A monolayer and thereby is chemisorbed and forms a second monolayer. This second monolayer displays a surface which is reactive only to Species A. Non-chemisorbed Species B, as well as displaced ligands and other byproducts of the reaction are then purged and the steps are repeated with exposure of the Species B monolayer to vaporized Species A. Optionally, the second species can react with the first species, but not chemisorb additional material thereto. That is, the second species can cleave some portion of the chemisorbed first species, altering such monolayer without forming another monolayer thereon, but leaving reactive sites available for formation of subsequent monolayers. In other ALD processes, a third species or more may be successively chemisorbed (or reacted) and purged just as described for the first and second species, with the understanding that each introduced species reacts with the monolayer produced immediately prior to its introduction. Optionally, the second species (or third or subsequent) can include at least one reaction gas if desired.

Thus, the use of ALD provides the ability to improve the control of thickness, composition, and uniformity of metal-containing layers on a substrate. For example, depositing thin layers of metal-containing compound in a plurality of cycles provides a more accurate control of ultimate film thickness. This is particularly advantageous when the precursor composition is directed to the substrate and allowed to chemisorb thereon, preferably further including at least one reaction gas that reacts with the chemisorbed species on the substrate, and even more preferably wherein this cycle is repeated at least once.

Purging of excess vapor of each species following deposition/chemisorption onto a substrate may involve a variety of techniques including, but not limited to, contacting the substrate and/or monolayer with an inert carrier gas and/or lowering pressure to below the deposition pressure to reduce the concentration of a species contacting the substrate and/or chemisorbed species. Examples of carrier gases, as discussed above, may include $N_2$, Ar, He, etc. Additionally, purging may instead include contacting the substrate and/or monolayer with any substance that allows chemisorption by-products to desorb and reduces the concentration of a contacting species preparatory to introducing another species. The contacting species may be reduced to some suitable concentration or partial pressure known to those skilled in the art based on the specifications for the product of a particular deposition process.

ALD is often described as a self-limiting process, in that a finite number of sites exist on a substrate to which the first species may form chemical bonds. The second species might only react with the surface created from the chemisorption of the first species and thus, may also be self-limiting. Once all of the finite number of sites on a substrate are bonded with a first species, the first species will not bond to other of the first species already bonded with the substrate. However, process conditions can be varied in ALD to promote such bonding and render ALD not self-limiting, e.g., more like pulsed CVD. Accordingly, ALD may also encompass a species forming other than one monolayer at a time by stacking of a species, forming a layer more than one atom or molecule thick.

The described method indicates the "substantial absence" of the second precursor (i.e., second species) during chemisorption of the first precursor since insignificant amounts of the second precursor might be present. According to the knowledge and the preferences of those with ordinary skill in the art, a determination can be made as to the tolerable amount of second precursor and process conditions selected to achieve the substantial absence of the second precursor.

Thus, during the ALD process, numerous consecutive deposition cycles are conducted in the deposition chamber, each cycle depositing a very thin metal-containing layer (usually less than one monolayer such that the growth rate on average is 0.2 to 3.0 Angstroms per cycle), until a layer of the desired thickness is built up on the substrate of interest. The layer deposition is accomplished by alternately introducing (i.e., by pulsing) precursor composition(s) into the deposition chamber containing a substrate, chemisorbing the precursor composition(s) as a monolayer onto the substrate surfaces, purging the deposition chamber, then introducing to the chemisorbed precursor composition(s) reaction gases and/or other precursor composition(s) in a plurality of deposition cycles until the desired thickness of the metal-containing layer is achieved. Preferred thicknesses of the metal-containing layers of the present invention are at least 1 angstrom (Å), more preferably at least 5 Å, and more preferably at least 10 Å. Additionally, preferred film thicknesses are typically no greater than 500 Å, more preferably no greater than 400 Å, and more preferably no greater than 300 Å.

The pulse duration of precursor composition(s) and inert carrier gas(es) is generally of a duration sufficient to saturate the substrate surface. Typically, the pulse duration is at least 0.1, preferably at least 0.2 second, and more preferably at least 0.5 second. Preferred pulse durations are generally no greater than 5 seconds, and preferably no greater than 3 seconds.

In comparison to the predominantly thermally driven CVD, ALD is predominantly chemically driven. Thus, ALD may advantageously be conducted at much lower temperatures than CVD. During the ALD process, the substrate temperature may be maintained at a temperature sufficiently low to maintain intact bonds between the chemisorbed precursor composition(s) and the underlying substrate surface and to prevent decomposition of the precursor composition(s). The temperature, on the other hand, must be sufficiently high to avoid condensation of the precursor composition(s). Typically the substrate is kept at a temperature of at least 25° C., preferably at least 150° C., and more preferably at least 200° C. Typically the substrate is kept at a temperature of no greater than 400° C., preferably no greater than 300° C., and more preferably no greater than 250° C., which, as discussed above, is generally lower than temperatures presently used in typical CVD processes. Thus, the first species or precursor composition is chemisorbed at this temperature. Surface reaction of the second species or precursor composition can occur at substantially the same temperature as chemisorption of the first precursor or, optionally but less preferably, at a substantially different temperature. Clearly, some small variation in temperature, as judged by those of ordinary skill, can occur but still be considered substantially the same temperature by providing a reaction rate statistically the same as would occur at the temperature of the first precursor chemisorption. Alternatively, chemisorption and subsequent reactions could instead occur at substantially exactly the same temperature.

For a typical vapor deposition process, the pressure inside the deposition chamber is at least $10^{-8}$ torr ($1.3 \times 10^{-6}$ Pa), preferably at least $10^{-7}$ torr ($1.3 \times 10^{-5}$ Pa), and more preferably at least $10^{-6}$ torr ($1.3 \times 10^{-4}$ Pa). Further, deposition pressures are typically no greater than 10 torr ($1.3 \times 10^{3}$ Pa), preferably no greater than 1 torr ($1.3 \times 10^{2}$ Pa), and more preferably no greater than $10^{-1}$ torr (13 Pa). Typically, the deposition chamber is purged with an inert carrier gas after the vaporized precursor composition(s) have been introduced into the chamber and/or reacted for each cycle. The inert carrier gas/gases can also be introduced with the vaporized precursor composition(s) during each cycle.

The reactivity of a precursor composition can significantly influence the process parameters in ALD. Under typical CVD process conditions, a highly reactive compound may react in the gas phase generating particulates, depositing prematurely on undesired surfaces, producing poor films, and/or yielding poor step coverage or otherwise yielding non-uniform deposition. For at least such reason, a highly reactive compound might be considered not suitable for CVD. However, some compounds not suitable for CVD are superior ALD precursors. For example, if the first precursor is gas phase reactive with the second precursor, such a combination of compounds might not be suitable for CVD, although they could be used in ALD. In the CVD context, concern might also exist regarding sticking coefficients and surface mobility, as known to those skilled in the art, when using highly gas-phase reactive precursors, however, little or no such concern would exist in the ALD context.

After layer formation on the substrate, an annealing process may be optionally performed in situ in the deposition chamber in a reducing, inert, plasma, or oxidizing atmosphere. Preferably, the annealing temperature is at least 400° C., more preferably at least 600° C. The annealing temperature is preferably no greater than 1000° C., more preferably no greater than 750° C., and even more preferably no greater than 700° C.

The annealing operation is preferably performed for a time period of at least 0.5 minute, more preferably for a time period of at least 1 minute. Additionally, the annealing operation is preferably performed for a time period of no greater than 60 minutes, and more preferably for a time period of no greater than 10 minutes.

One skilled in the art will recognize that such temperatures and time periods may vary. For example, furnace anneals and rapid thermal annealing may be used, and further, such anneals may be performed in one or more annealing steps.

As stated above, the use of the compounds and methods of forming films of the present invention are beneficial for a wide variety of thin film applications in semiconductor structures, particularly those using high dielectric materials. For example, such applications include gate dielectrics and capacitors such as planar cells, trench cells (e.g., double sidewall trench capacitors), stacked cells (e.g., crown, V-cell, delta cell, multi-fingered, or cylindrical container stacked capacitors), as well as field effect transistor devices.

A system that can be used to perform vapor deposition processes (chemical vapor deposition or atomic layer deposition) of the present invention is shown in FIG. 1. The system includes an enclosed vapor deposition chamber 10, in which a vacuum may be created using turbo pump 12 and backing pump 14. One or more substrates 16 (e.g., semiconductor substrates or substrate assemblies) are positioned in chamber 10. A constant nominal temperature is established for substrate 16, which can vary depending on the process used. Substrate 16 may be heated, for example, by an electrical resistance heater 18 on which-substrate 16 is mounted. Other known methods of heating the substrate may also be utilized.

In this process, precursor compositions as described herein, 60 and/or 61, are stored in vessels 62. The precursor composition(s) are vaporized and separately fed along lines 64 and 66 to the deposition chamber 10 using, for example, an inert carrier gas 68. A reaction gas 70 may be supplied along line 72 as needed. Also, a purge gas 74, which is often the same as the inert carrier gas 68, may be supplied along line 76 as needed. As shown, a series of valves 80-85 are opened and closed as required.

The following examples are offered to further illustrate various specific embodiments and techniques of the present invention. It should be understood, however, that many variations and modifications understood by those of ordinary skill in the art may be made while remaining within the scope of the present invention. Therefore, the scope of the invention is not intended to be limited by the following example. Unless specified otherwise, all percentages shown in the examples are percentages by weight.

EXAMPLES

Example 1

Synthesis and Characterization of a Ligand Source of Formula III, with $R^1=R^5$=sec-butyl; $R^2=R^4$=methyl; and $R^3$=H: N-sec-butyl-(4-sec-butylimino)-2-penten-2-amine An oven-dry 1-L Schlenk flask fitted with addition funnel was charged with 101 mL of sec-butylamine and 200 mL dichloromethane. The addition funnel was then charged with 103 mL of 2,4-pentanedione and 400 mL dichloromethane, which were then added dropwise to the solution in the Schlenk flask. The resulting solution was then stirred for 90 hours. The aqueous phase formed during the reaction was then separated and extracted with 2×50 mL portions of diethyl ether. The combined organic fractions were dried over anhydrous sodium sulfate and concentrated on a rotary evaporator. The concentrate was then distilled at 66° C., 0.7 Torr (93 Pa); the distillate was a clear colorless liquid. 108.4 g were collected for 70% yield. Gas chromatographic/mass spectrometric (GC/MS) analysis of the distillate indicated a compound with an apparent purity of 99.9% having a mass spectrum consistent with N-sec-butyl-4-amino-3-penten-2-one.

An oven-dry 500-mL Schlenk flask was charged with 38.0 g of triehyloxonium tetrafluoroborate (0.2 mol) under argon atmosphere and fitted with an addition funnel. 200 mL of dichloromethane was added to form a clear colorless solution. A 60 mL portion of dichloromethane and 31.05 grams of N-sec-butyl-4-amino-3-penten-2-one (0.2 mol) were charged into the addition funnel and this solution was added dropwise to the solution in the Schlenk flask, and the resulting solution was then stirred for 30 minutes. A solution of 20.2 mL sec-butyl amine (0.2 mol) and 30 mL dichloromethane was charged into the addition funnel and added to the reaction solution, which was then stirred overnight. Volatiles were then removed in vacuo and the resulting yellow oily solid was washed with 60 mL aliquot of cold ethyl acetate while the flask was placed in an ice-bath. No solid precipitate was observed due to this wash; rather part of the crude product appeared to dissolve. After decanting off the ethyl acetate wash, a second 60 mL ethyl acetate wash was attempted with identical results. Combined washes and crude product were added to a mixture of 500 mL benzene and 500 mL water containing 8.0 g sodium hydroxide (0.2 mol). The mixture was stirred for three minutes and then the organic phase was separated. The aqueous phase was extracted four times, each with 100 mL diethyl ether portions. All the organic phases were combined, dried over sodium sulfate and concentrated on a rotary evaporator. The crude product was then distilled through a 20 cm glass-bead packed column and short path still head. The desired product was collected in ≧99% pure form at 60-63° C., 80 mTorr (10 Pa) pressure. The apparent purity was determined by GC/MS, where the only impurity observed was N-sec-butyl-4-amino-3-penten-2-one.

Example 2

Synthesis and Characterization of a Metal-Containing Compound of Formula I, with M=Sr (n=2); $R^1$=$R^5$=sec-butyl; $R^2$=$R^4$=methyl; $R^3$=H; x=2; and z=0: Strontium bis(N-sec-butyl-(4-sec-butyl-imino)-2-penten-2-aminato).

In a dry box, a 500 mL Schlenk flask was charged with 7.765 g of strontium bis(hexamethyldisilazane) (19 mmol) and 50 mL toluene. A second Schlenk flask was charged with 8.000 g of N-sec-butyl-(4-sec-butylimino)-2-penten-2-amine (38 mmol) and 50 mL toluene. The ligand solution was added to the strontium solution, immediately producing an amber-colored reaction solution which was stirred for 18 hours. Volatiles were then removed in vacuo. The crude product, a brown liquid, was charged into a 50 mL round-bottom Schlenk flask fitted with short path still head and Schlenk receiver flask in the dry box. The distillation apparatus was attached to a vacuum line and evacuated further, which induced some solidification in the still pot. At full vacuum, heating of the still pot was begun. A clear liquid (approximately 0.5 g) was collected at 60° C.; GC/MS confirmed this material to be the ligand precursor. A second receiver flask was attached and the product was distilled at 145-160° C. at full vacuum. The "cooling lines" to the still head were filled with 90° C. ethylene glycol to prevent the condensing distillate from becoming too viscous and clogging the still path. The collected product formed a yellow, slightly oily solid upon cooling. 6.585 g were collected for 71.6% yield. Elemental analysis calculated for $C_{26}H_{50}N_4Sr$: Sr, 17.3%. Found 16.6%. Melting point of distilled product was determined to be 44-48° C.

$^1$H and $^{13}$C nuclear magnetic resonance (NMR) results were consistent with the presence of four diastereomeric forms of the compound (two enantiomeric pairs and two meso forms). $^1$H NMR ($C_6D_6$, δ): 4.190 (m, 2H, J=2.4, 2.4 Hz, β-C—H), 3.330 (m, 4H, J=6.3 Hz, N—CH(CH$_3$)(CH$_2$CH$_3$)), 1.873 (d, 12H, J=2.4 Hz, α-C—CH$_3$), 1.506 (m, 8H, J=1.4, 6.4 Hz, N—CH(CH$_3$)(CH$_2$CH$_3$)), 1.253-1.220 (d, 4 sets overlapping, 6H, J=6.15-6.45 Hz, N—CH(CH$_3$)(CH$_2$CH$_3$)), 1.188-1.162 (d, 4 sets overlapping, 6H, J=6.15-6.45 Hz, N—CH(CH$_3$)(CH$_2$CH$_3$)), 0.970-0.897 (d, 4 sets overlapping, 12H, J=6.2 Hz, N—CH(CH$_3$)(CH$_2$CH$_3$)). $^{13}$C NMR ($C_6D_6$, δ): 161.294, 161.226 (α-C—CH$_3$); 94.80, 86.96, 86.89, 86.70 (β-CH); 56.19, 56.00, 52.67, 52.58 (N—CH(CH$_3$)(CH$_2$CH$_3$)); 33.61, 33.56, 32.13, 32.04 (N—CH(CH$_3$)(CH$_2$CH$_3$)); 23.86, 23.78, 23.67 (α-C—CH$_3$); 22.47, 22.39 (N—CH(CH$_3$)(CH$_2$CH$_3$)); 11.63, 11.33, 10.81, 10.75 (N—CH(CH$_3$)(CH$_2$CH$_3$)).

Figure 2:
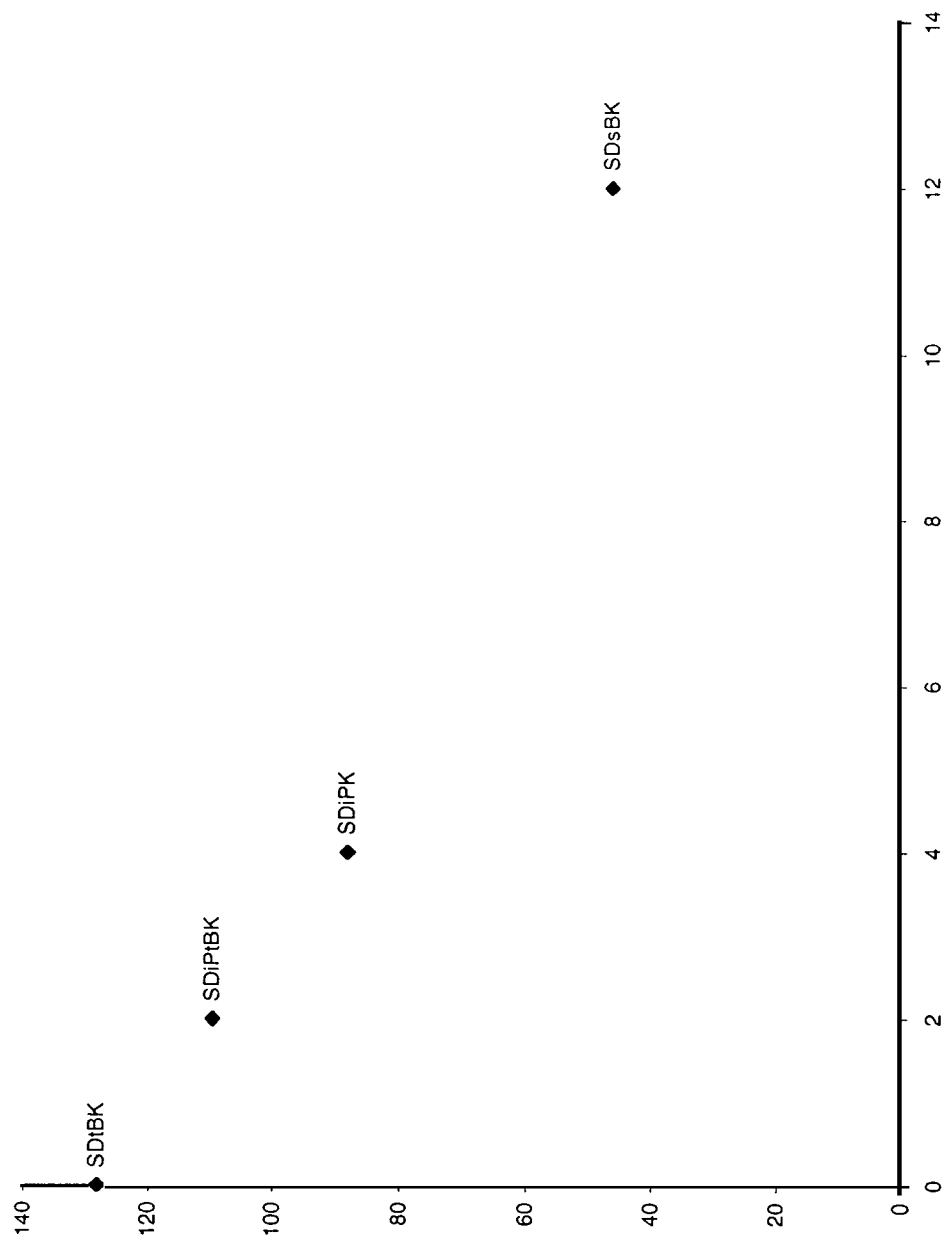
FIG. 2 is a graphical representation of degrees of freedom (x-axis) vs. melting point (° C.; y-axis) for various metal-containing compounds having at least one β-diketiminate ligand, which illustrates decreasing melting point for increasing degrees of freedom. Degrees of freedom were quantified by a method described by Li et al. in *Inorganic Chemistry*, 44:1728-1735 (2005), and as further described herein. SDtBK represents a metal-containing compound of Formula I having zero degrees of freedom, wherein M=Sr (n=2), $R^1$=$R^5$=tert-butyl, $R^2$=$R^4$=methyl, $R^3$=H, x=2, and z=0. SDiPtBK represents a metal-containing compound of Formula I having 2 degrees of freedom (2 isopropyls), wherein M=Sr (n=2), $R^1$=isopropyl (1 degree of freedom), $R^5$=tert-butyl, $R^2$=$R^4$=methyl, $R^3$=H, x=2, and z=0. SDiPK represents a metal-containing compound of Formula I having 4 degrees of freedom (4 isopropyls), wherein M=Sr (n=2), $R^1$=$R^5$=isopropyl (each isopropyl having 1 degree of freedom), $R^2$=$R^4$=methyl, $R^3$=H, x=2, and z=0. SDsBK represents a metal-containing compound of Formula I having 12 degrees of freedom (4 sec-butyls), wherein M=Sr (n=2), $R^1$=$R^5$=sec-butyl (each sec-butyl having 3 degrees of freedom), $R^2$=$R^4$=methyl, $R^3$=H, x=2, and z=0. The melting point for SDsBK (44-48° C.) is disclosed herein in Example 2. The melting points for SDtBK (127-129° C.) and SDiPK (87-89° C.) have been disclosed in El-Kaderi et al., *Organometallics*, 23:4995-5002 (2004). The melting point for SDiPtBK (see, copending U.S. application Ser. No. 11/169,082, entitled "UNSYMMETRICAL LIGAND SOURCES, REDUCED SYMMETRY METAL-CONTAINING COMPOUNDS, AND SYSTEMS AND METHODS INCLUDING SAME," filed on the same day herewith) was measured as 109.5° C.

As illustrated in FIG. 2, the metal-containing compound having the formula (Formula I) where $R^1$=$R^5$=sec-butyl (3 degrees of freedom for sec-butyl as quantified, for example, in Table 1) has a lower melting point (44-48° C.) compared to disclosed melting points for the corresponding metal-containing compounds having the formula (Formula I) (see, El-Kaderi et al., *Organometallics*, 23:4995-5002 (2004)) where $R^1$=$R^5$=isopropyl (87-89° C.; 1 degree of freedom for isopropyl as quantified, for example, in Table 1); and where $R^1$=$R^5$=tert-butyl (127-129° C.; 0 degrees of freedom for tert-butyl as quantified, for example, in Table 1).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the formula (Formula I):

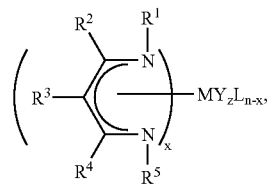

wherein:

M is selected from the group consisting of a Group 2 metal, a Group 3 metal, a Lanthanide, and combinations thereof;

each L is independently an anionic ligand;

each Y is independently a neutral ligand;

n represents the valence state of the metal;

z is from 0 to 10;

x is from 1 to n; and each $R^1$, $R^2$, $R^3$, $R^4$, and $R^5$ is independently hydrogen or an organic group with the proviso that at least one of the R groups is a fluorine-containing organic group.

2. The compound of claim 1 wherein each $R^1$, $R^2$, $R^3$, $R^4$, and $R^5$ is independently hydrogen or an organic group having 1 to 10 carbon atoms.

3. The compound of claim 1 wherein M is selected from the group consisting of Ca, Sr, Ba, and combinations thereof.

4. The compound of claim 1 wherein at least one L is selected from the group consisting of a halide, an alkoxide group, an amide group, a mercaptide group, cyanide, an alkyl group, an amidinate group, a guanidinate group, an isoureate group, a β-diketonate group, a β-iminoketonate group, a β-diketiminate group, and combinations thereof.

5. The compound of claim 4 wherein the at least one L is a β-diketiminate group having a structure that is the same as that of the β-diketiminate ligand shown in Formula I.

6. The compound of claim 4 wherein the at least one L is a β-diketiminate group having a structure that is different than that of the β-diketiminate ligand shown in Formula I.

7. The compound of claim 1 wherein at least one Y is selected from the group consisting of a carbonyl, a nitrosyl, ammonia, an amine, nitrogen, a phosphine, an alcohol, water, tetrahydrofuran, and combinations thereof.

8. A method of making a metal-containing compound, the method comprising combining components comprising:

a ligand source of the formula (Formula III):

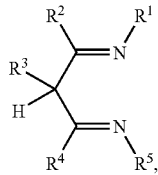

a tautomer thereof, or a deprotonated conjugate base or metal complex thereof;

optionally a source for an anionic ligand L;

optionally a source for a neutral ligand Y; and a metal (M) source;

wherein each $R^1$, $R^2$, $R^3$, $R^4$, and $R^5$ is independently hydrogen or an organic group with the proviso that at least one of the R groups is a fluorine-containing organic group; and wherein the metal (M) source is selected from the group consisting of a Group 2 metal source, a Group 3 metal source, a Lanthanide metal source, and combinations thereof, under conditions sufficient to provide a metal-containing compound of the formula (Formula I):

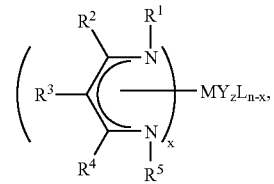

wherein M, L, Y, $R^1$, $R^2$, $R^3$, $R^4$, and $R^5$ are as defined above, n represents the valence state of the metal, z is from 0 to 10, and x is from 1 to n.

9. The method of claim 8 wherein the metal (M) source comprises a M(0), a M(II) halide, a M(II) pseudohalide, a M(II) amide, or combinations thereof.

10. The method of claim 8 wherein M is selected from the group consisting of Ca, Sr, Ba, and combinations thereof.

11. A compound of the formula (Formula I):

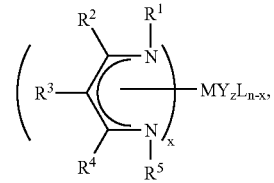

wherein:

M is selected from the group consisting of a Group 2 metal, a Group 3 metal, a Lanthanide, and combinations thereof;

each L is independently an anionic ligand;

each Y is independently a neutral ligand;

n represents the valence state of the metal;

z is from 0 to 10;

x is from 1 to n; and each $R^1$, $R^2$, $R^3$, $R^4$, and $R^5$ is independently hydrogen or an aliphatic group having 1 to 5 carbon atoms, with the proviso that at least one of $R^2$, $R^3$, and $R^4$ is a moiety selected from the group consisting of ethyl, n-propyl, isopropyl, n-butyl, sec-butyl, isobutyl, n-pentyl, 2-pentyl, 3-pentyl, 2-methyl-1-butyl, 3-methyl-2-butyl, isopentyl, tert-pentyl, and neopentyl.

12. The compound of claim 11 wherein M is selected from the group consisting of Ca, Sr, Ba, and combinations thereof.

13. A method of making a metal-containing compound, the method comprising combining components comprising:

a ligand source of the formula (Formula III):

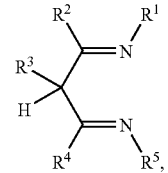

a tautomer thereof, or a deprotonated conjugate base or metal complex thereof;

optionally a source for an anionic ligand L;

optionally a source for a neutral ligand Y; and a metal (M) source;

wherein each $R^1$, $R^2$, $R^3$, $R^4$, and $R^5$ is independently hydrogen or an aliphatic group having 1 to 5 carbon atoms, with the proviso that at least one of $R^2$, $R^3$, and $R^4$ is a moiety selected from the group consisting of ethyl, n-propyl, isopropyl, n-butyl, sec-butyl, isobutyl, n-pentyl, 2-pentyl, 3-pentyl, 2-methyl-1butyl, 3-methyl-2-butyl, isopentyl, tert-pentyl, and neopentyl; and wherein the metal (M) source is selected from the group consisting of a Group 2 metal source, a Group 3 metal source, a Lanthanide metal source, and combinations thereof, under conditions sufficient to provide a metal-containing compound of the formula (Formula I):

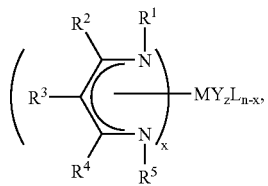

wherein M, L, Y, $R^1$, $R^2$, $R^3$, $R^4$, and $R^5$ are as defined above, n represents the valence state of the metal, z is from 0 to 10, and x is from 1 to n.

14. The method of claim 13 wherein the metal (M) source comprises a M(0), a M(II) halide, a M(II) pseudohalide, a M(II) amide, or combinations thereof.

15. The method of claim 13 wherein M is selected from the group consisting of Ca, Sr, Ba, and combinations thereof.

16. A compound of the formula (Formula I):

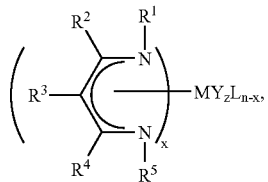

wherein:
M is selected from the group consisting of a Group 2 metal, a Group 3 metal, a Lanthanide, and combinations thereof;
each L is independently an anionic ligand;
each Y is independently a neutral ligand;
n represents the valence state of the metal;
z is from 0 to 10;
x is from 1 to n; and
each $R^1$, $R^2$, $R^3$, $R^4$, and $R^5$ is independently hydrogen or an aliphatic group having 1 to 5 carbon atoms, with the proviso that at least one of $R^1$ and $R^5$ is a moiety selected from the group consisting of n-propyl, n-butyl, sec-butyl, isobutyl, n-pentyl, 2-pentyl, 3-pentyl, 2-methyl-1-butyl, 3-methyl-2-butyl, isopentyl, and tert-pentyl.

17. The compound of claim 16 wherein M is selected from the group consisting of Ca, Sr, Ba, and combinations thereof.

18. A method of making a metal-containing compound, the method comprising combining components comprising:
a ligand source of the formula (Formula III):

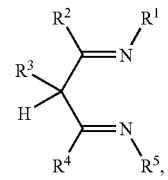

a tautomer thereof, or a deprotonated conjugate base or metal complex thereof;
optionally a source for an anionic ligand L;
optionally a source for a neutral ligand Y; and
a metal (M) source;
wherein each $R^1$, $R^2$, $R^1$, $R^4$, and $R^5$ is independently hydrogen or an aliphatic group having 1 to 5 carbon atoms, with the proviso that at least one of $R^1$ and $R^5$ is a moiety selected from the group consisting of n-propyl, n-butyl, sec-butyl, isobutyl, n-pentyl, 2-pentyl, 3-pentyl, 2-methyl-1-butyl, 3-methyl-2-butyl, isopentyl, and tert-pentyl; and
wherein the metal (M) source is selected from the group consisting of a Group 2 metal source, a Group 3 metal source, a Lanthanide metal source, and combinations thereof, under conditions sufficient to provide a metal-containing compound of the formula (Formula I):

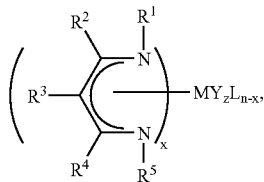

wherein M, L, Y, $R^1$, $R^2$, $R^3$, $R^4$, and $R^5$ are as defined above, n represents the valence state of the metal, z is from 0 to 10, and x is from 1 to n.

19. The method of claim 18 wherein the metal (M) source comprises a M(0), a M(II) halide, a M(II) pseudohalide, a M(II) amide, or combinations thereof.

20. The method of claim 18 wherein M is selected from the group consisting of Ca, Sr, Ba, and combinations thereof.

* * * * *

UNITED STATES PATENT AND TRADEMARK OFFICE
CERTIFICATE OF CORRECTION

PATENT NO. : 7,439,338 B2　　　　　　　　　　　　　　　　　　　Page 1 of 1
APPLICATION NO. : 11/169065
DATED : October 21, 2008
INVENTOR(S) : Millward et al.

It is certified that error appears in the above-identified patent and that said Letters Patent is hereby corrected as shown below:

On the Title page, in field (56), under "Other Publications", in column 2, line 36, delete "2,6i" and insert -- 2,6-i --, therefor.

In column 33, line 6, in Claim 13, delete "1butyl," and insert -- 1-butyl, --, therefor.

In column 34, line 24, in Claim 18, after "$R^2$," delete "$R^1$," and insert -- $R^3$, --, therefor.

Signed and Sealed this

Thirteenth Day of January, 2009

JON W. DUDAS
*Director of the United States Patent and Trademark Office*